United States Patent
Hagiya et al.

(10) Patent No.: US 7,820,802 B2
(45) Date of Patent: Oct. 26, 2010

(54) AZODICARBOXYLIC ACID BIS(2-ALKOXYETHYL) ESTER COMPOUND, AND PRODUCTION INTERMEDIATE THEREOF

(76) Inventors: Kazutake Hagiya, c/o Chemicals Research Center of Toyo Kasei Kogyo Co., Ltd., 2900, Sone-cho, Takasago, Hyogo (JP) 676-0082; Takashi Sugimura, 31-802, Yasuda 2-chome, Himeji, Hyogo (JP) 670-0955

( * ) Notice: Subject to any disclaimer, the term of this patent is extended or adjusted under 35 U.S.C. 154(b) by 0 days.

(21) Appl. No.: 12/443,861

(22) PCT Filed: Jan. 30, 2008

(86) PCT No.: PCT/JP2008/051359

§ 371 (c)(1),
(2), (4) Date: Apr. 1, 2009

(87) PCT Pub. No.: WO2008/093702

PCT Pub. Date: Aug. 7, 2008

(65) Prior Publication Data

US 2010/0048881 A1    Feb. 25, 2010

(30) Foreign Application Priority Data

Jan. 31, 2007   (JP) .............................. 2007-052027
Sep. 27, 2007   (JP) .............................. 2007-252331

(51) Int. Cl.
*C07C 243/14* (2006.01)
*C07C 245/04* (2006.01)

(52) U.S. Cl. ..................... 534/586; 534/886; 560/155; 560/158; 560/169

(58) Field of Classification Search ................. 534/886
See application file for complete search history.

(56) References Cited

U.S. PATENT DOCUMENTS

| | | | | |
|---|---|---|---|---|
| 2,533,189 A | * | 12/1950 | Flory et al. | 560/158 |
| 2,554,141 A | * | 5/1951 | Flory et al. | 534/829 |
| 2,903,361 A | * | 9/1959 | Marks et al. | 426/26 |
| 3,017,406 A | * | 1/1962 | Mehr | 534/586 |
| 3,192,196 A | * | 6/1965 | Vidal et al. | 534/586 |
| 3,306,862 A | * | 2/1967 | Schack et al. | 521/60 |
| 3,347,845 A | * | 10/1967 | Sheppard et al. | 534/576 |
| 3,488,342 A | * | 1/1970 | Van Leeuwen et al. | 534/586 |
| 6,153,633 A | * | 11/2000 | Ghosh et al. | 514/372 |
| 2009/0318720 A1 | * | 12/2009 | Otten | 552/592 |

FOREIGN PATENT DOCUMENTS

JP         54-41970 A         4/1979

OTHER PUBLICATIONS

J. C. Kauer, "Ethyl Azodicarboxylate", Organic Synthesis Collective, vol. 4, 1963, p. 411-415.
A. P. Dobbs et al., Synthesis of fluorous azodicarboxylates: towards cleaner Mitsunobu reactions, Tetrahedron Letters, 2002, vol. 43, p. 2807-2810.
Zhang Li-Jie et al., Study on Dead-catalyzed H2O2 Oxidations of Potassium Penicillin G, Chinese J. Antibiotics, 2003, vol. 28, No. 7, p. 391-393, 402.
Mitsunobu Oya, The Use of Diethyl Azodicarboxylate and Triphenylphosphine in Synthesis and Transformation of Natural Products, Synthesis, 1981, No. 1, p. 1-28.
Takashi Sugimura et al., "Di-2-methoxyethyl Azodicarboxylate (DMEAD): An Inexpensive and Separation—friendly Alternative Reagent for the Mitsunobu Reaction", Chemistry Letters, vol. 36, No. 4, Apr. 5, 2007, p. 566-567.

* cited by examiner

*Primary Examiner*—Fiona T Powers
(74) *Attorney, Agent, or Firm*—Marvin A. Motsenbocker; Mots Law, PLLC

(57) ABSTRACT

Provided is an industrially safe and useful azodicarboxylic acid bis(2-alkoxyethyl) ester compound that is useful for the Mitsunobu reaction in which it is used in combination with a phosphorus compound to carry out a dehydration condensation reaction, and also useful as an oxidizing agent, and a starting material for various synthetic processes. Also provided are a production intermediate of the above-described compound, and methods for producing these compounds. An azodicarboxylic acid bis(2-alkoxyethyl) ester compound represented by formula (1);

[Chem. 1]

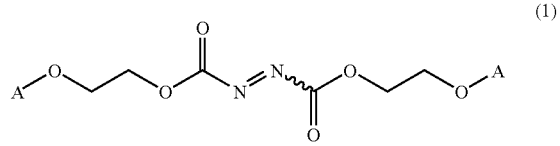

(1)

wherein A represents an alkyl group having 1 to 10 carbon atoms.

4 Claims, No Drawings

AZODICARBOXYLIC ACID BIS(2-ALKOXYETHYL) ESTER COMPOUND, AND PRODUCTION INTERMEDIATE THEREOF

TECHNICAL FIELD

The present invention relates to a novel azodicarboxylic acid bis(2-alkoxyethyl) ester compound that is industrially safe and useful, a production intermediate thereof, and methods for producing these compounds.

BACKGROUND ART

The Mitsunobu reaction in which a phosphorus compound and an azodicarboxylic acid diester are used to carry out dehydration condensation have been employed as a useful synthetic reaction for producing medical drugs and the like. The Mitsunobu reaction is known as a dehydration condensation reaction between alcohols and a variety of acidic compounds such as carboxylic acid compounds, phenolic compounds, imide compounds, phosphoric acid compounds and hydrogen azide, and it is also known that use of an optically active alcohol as a starting material can provide the desired product as a result of complete stereo inversion (see Non-patent Document 1).

However, known azodicarboxylic acid dimethyl ester, azodicarboxylic acid diethyl ester, and azodicarboxylic acid diisopropyl ester have the following disadvantages.

(1) Since these compounds are liquid at ordinary temperatures, purification by distillation must be performed. However, azo compounds are generally unstable in heat, and it is therefore dangerous to heat these compounds. In fact, it has been demonstrated that caution should be exercised when synthesizing azodicarboxylic acid dimethyl ester and azodicarboxylic acid diethyl ester (see Non-patent Document 2).

(2) For example, when a Mitsunobu reaction in which dehydration condensation is carried out in combination with a phosphorus compound, or an oxidation reaction is performed, 1,2-hydrazinedicarboxylic acid diester is produced as a by-product; this compound is insoluble in water and moderately dissolves in an organic solvent, and therefore, many processes are required to remove or separate this compound from the product.

Therefore, at present, conventional azodicarboxylic acid diester compounds are not industrially advantageous compounds due to the above-described disadvantages.

Non-patent Document 1: Synthesis, 1, 1 (1981) (*Syntheis*, 1st ed., p. 1, 1981)

Non-patent Document 2: *Org. Synth. Coll.*, Vol. IV, 411 (1963)

DISCLOSURE OF INVENTION

Problem to be Solved by the Invention

The present invention solves the above-described problems of the conventional art, and provides an industrially safe and useful azodicarboxylic acid bis(2-alkoxyethyl) ester compound that is useful for the Mitsunobu reaction in which it is used in combination with a phosphorus compound to perform dehydration condensation, and also useful as an oxidizing agent, and a starting material for various synthesis processes. The invention also provides a production intermediate of the above-described compound, and methods for producing these compounds.

Means for Solving Problem

As a result of extensive studies for solving the above-described problems, the present inventors found a crystalline azodicarboxylic acid bis(2-alkoxyethyl) ester compound that does not require purification by distillation, and a method for producing the compound. The inventors also found that a 1,2-hydrazinedicarboxylic acid bis(2-alkoxyethyl) ester compound produced as a by-product when using the above-described azodicarboxylic acid bis(2-alkoxyethyl) ester compound in a Mitsunobu reaction in which the azodicarboxylic acid bis(2-alkoxyethyl) ester compound is used in combination with a phosphorus compound to carry out dehydration condensation, or in an oxidation reaction, or the like, dissolves in water and thus can be easily removed, and thereby the present invention was achieved.

More specifically, the present invention provides an azodicarboxylic acid bis(2-alkoxyethyl) ester compound as shown below, a production intermediate thereof, and methods for producing these compounds.

Item 1. An azodicarboxylic acid bis(2-alkoxyethyl) ester compound represented by formula (1):

[Chem. 1]

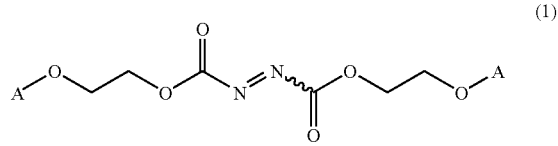

(1)

wherein A represents an alkyl group having 1 to 10 carbon atoms.

Item 2. The compound according to Item 1, wherein the alkyl group is a methyl group.

Item 3. A method for producing an azodicarboxylic acid bis(2-alkoxyethyl) ester compound, comprising the steps of:

(a): reacting hydrazine with a halocarbonic acid (2-alkoxyethyl) ester compound represented by formula (2):

[Chem. 2]

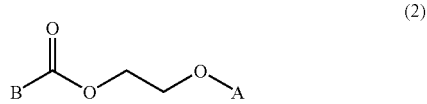

(2)

wherein A represents an alkyl group having 1 to 10 carbon atoms, and B represents a halogen atom, to give a 1,2-hydrazinedicarboxylic acid bis(2-alkoxyethyl) ester compound represented by formula (3):

[Chem. 3]

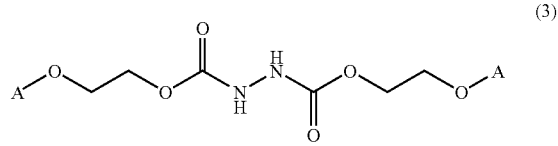

(3)

wherein A is as defined above; and (b): oxidizing the 1,2-hydrazinedicarboxylic acid bis(2-alkoxyethyl) ester compound represented by formula (3):

[Chem. 4]

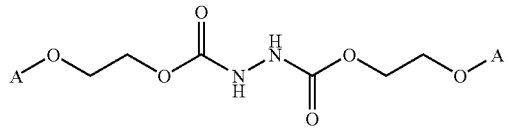

(3)

wherein A is as defined above, to give an azodicarboxylic acid bis(2-alkoxyethyl) ester compound represented by formula (1):

[Chem. 5]

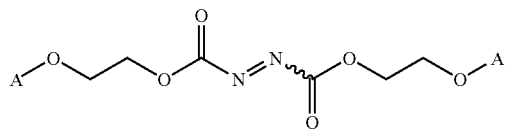

(1)

wherein A is as defined above.

Item 4. A 1,2-hydrazinedicarboxylic acid bis(2-alkoxyethyl) ester compound represented by formula (3):

[Chem. 6]

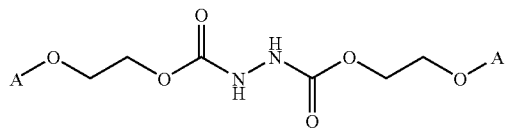

(3)

wherein A represents an alkyl group having 1 to 10 carbon atoms.

Item 5. The compound according to Item 4, wherein the alkyl group is a methyl group.

Item 6. A method for producing a 1,2-hydrazinedicarboxylic acid bis(2-alkoxyethyl) ester compound, comprising the step of:

(a): reacting hydrazine with a halocarbonic acid (2-alkoxyethyl) ester compound represented by formula (2):

[Chem. 7]

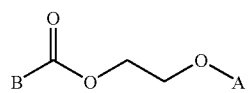

(2)

wherein A represents an alkyl group having 1 to 10 carbon atoms, and B represents a halogen atom, to give a 1,2-hydrazinedicarboxylic acid bis(2-alkoxyethyl) ester compound represented by formula (3):

[Chem. 8]

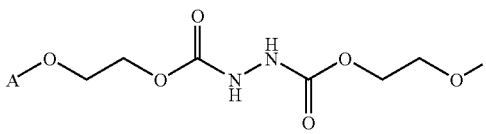

(3)

wherein A is as defined above.

EFFECTS OF THE INVENTION

According to the present invention, an azodicarboxylic acid bis(2-alkoxyethyl) ester compound represented by formula (1) can be produced more safely and the after-treatment therefor is easier compared with conventional azodicarboxylic acid esters, and it has a comparable reactivity and is thus an industrially highly advantageous compound.

DESCRIPTION OF THE INVENTION

Hereinafter, the present invention will be described in detail.

First, "A" in formulae (1), (2) and (3) will be described.

"A" is an alkyl group that may be linear or branched. In the case of a branched alkyl group, there is no particular limitation with respect to the position of branching and the number of branches. Those that have 1 to 10 carbon atoms are preferable, and those having 1 to 4 carbon atoms are more preferable. Preferable specific examples of the alkyl group include a methyl group, an ethyl group, an n-propyl group, an isopropyl group, an n-butyl group, a but-2-yl group, a 2-methylprop-1-yl group, and a 2-methylprop-2-yl group. A methyl group and an ethyl group are preferable, and a methyl group is particularly preferable.

Next, "B" in formula (2) will be described.

"B" is a halogen atom, without any particular limitations. Specific examples include fluorine, chlorine, bromine, and iodine. Chlorine and bromine are particularly preferable in terms of versatility and the like.

In the following, the steps (a) and (b) presented in Item 3 and Item 6 above will be described in detail.

[Step (a)]

This step is a step of reacting hydrazine with a halocarbonic acid 2-alkoxyethyl ester compound represented by formula (2) to give a 1,2-hydrazinedicarboxylic acid bis(2-alkoxyethyl) ester compound represented by formula (3).

The hydrazine and the halocarbonic acid (2-alkoxyethyl) ester compound represented by formula (2) may be produced by any method. Specific examples of the halocarbonic acid (2-alkoxyethyl) ester compound represented by formula (2) include fluorocarbonic acid (2-alkoxyethyl) ester, chlorocarbonic acid (2-alkoxyethyl) ester, bromocarbonic acid (2-alkoxyethyl) ester, and iodocarbonic acid (2-alkoxyethyl) ester. Among these, chlorocarbonic acid (2-alkoxyethyl) ester and bromocarbonic acid (2-alkoxyethyl) ester are preferable.

This reaction requires a base, and there is no particular limitation with respect to the kind of base. Specific preferable examples thereof include alkali metal salts such as lithium hydroxide, sodium hydroxide, potassium hydroxide, cesium hydroxide, lithium carbonate, sodium carbonate, potassium carbonate, and cesium carbonate; alkaline-earth metal salts such as magnesium hydroxide, calcium hydroxide, barium hydroxide, magnesium carbonate, calcium carbonate, and barium carbonate; and tertiary amines such as trimethylamine, triethylamine, tripropylamine, diisopropylethylamine, tributylamine, tripentylamine, trihexylamine, trioctylamine, triallylamine, pyridine, 2-methylpyridine, 3-methylpyridine, 4-methylpyridine, N-methylmorpholine, N,N-dimethylcyclohexylamine, N,N-dimethylaniline, N-methylimidazole, 1,4-diazabicyclo[2.2.2]octane, and 1,8-diazabicyclo[5.4.0]undec-7-ene. Among these, sodium carbonate, potassium carbonate, and triethylamine are particularly preferable. The amount of base used per mol of hydrazine is preferably 1.0 to 3.0 mol, more preferably 1.0 to 2.0 mol.

The amount of use per mol of hydrazine of the halocarbonic acid (2-alkoxyethyl) ester compound represented by formula (2) is preferably 2.0 to 5.0 mol, more preferably 2.0 to 3.0 mol.

There is no particular limitation with respect to the reaction solvent, as long as it will not impede the reaction. Preferable specific examples thereof include hydrocarbon solvents such as n-pentane, n-hexane, cyclohexane, n-heptane, and n-octane; ether solvents such as diethyl ether, diisopropyl ether, tetrahydrofuran, dimethoxyethane, cyclopentyl methyl ether, t-butyl methyl ether, and anisole; aromatic solvents such as benzene, toluene, and xylene; halogenated solvents such as dichloromethane, chloroform, carbon tetrachloride, dichloroethane, and dichloropropane; alcohol solvents such as methanol, ethanol, n-propanol, isopropanol, n-butanol, isobutanol, and t-butanol; and aqueous solvents. Among these, acetonitrile, tetrahydrofuran, methanol, ethanol, and water are particularly preferable. These solvents may be used alone or as a mixture. The amount of solvent used per gram of hydrazine is preferably 0.5 mL to 50 mL, more preferably 2 mL to 20 mL.

This reaction is performed by mixing, in a reaction solvent, hydrazine, a base, and a halocarbonic acid (2-alkoxyethyl) ester compound represented by formula (2). The reaction temperature is preferably −20° C. to 60° C., more preferably about 0° C. to 30° C., since too low a reaction temperature results in a low reaction rate, and too high a reaction temperature results in increased by-products. The reaction time is preferably 0.1 hour to 24 hours, more preferably about 0.5 hour to 3 hours.

When a 1,2-hydrazinedicarboxylic acid bis(2-alkoxyethyl) ester compound represented by formula (3) is in the form of crystals at the end of the reaction, filtration is performed, and purification is carried out by recrystallization or suspension washing, as needed. When the above-described compound is not crystallized, water is added to stop the reaction if a solvent other than water is used. Subsequently, an ordinary method such as extraction, washing, dehumidification, or solvent distillation is carried out to give a crude product which is then purified by, for example, crystallization, recrystallization, or column chromatography, to give a 1,2-hydrazinedicarboxylic acid bis(2-alkoxyethyl) ester compound represented by formula (3).

[Step (b)]

This step is a step of oxidizing the 1,2-hydrazinedicarboxylic acid bis(2-alkoxyethyl) ester compound represented by formula (3) to give a azodicarboxylic acid bis(2-alkoxyethyl) ester compound represented by formula (1).

The 1,2-hydrazinedicarboxylic acid bis(2-alkoxyethyl) ester compound represented by formula (3) may be produced by any method. Specific examples of the 1,2-hydrazinedicarboxylic acid bis(2-alkoxyethyl) ester compound represented by formula (3) include
1,2-hydrazinedicarboxylic acid bis(2-methoxyethyl) ester,
1,2-hydrazinedicarboxylic acid bis(2-ethoxyethyl) ester,
1,2-hydrazinedicarboxylic acid bis(2-propoxyethyl) ester,
1,2-hydrazinedicarboxylic acid bis(2-butoxyethyl) ester,
1,2-hydrazinedicarboxylic acid bis(2-(but-2-oxy)ethyl) ester,
1,2-hydrazinedicarboxylic acid bis(2-(2-methylprop-1-oxy) ethyl) ester,
and 1,2-hydrazinedicarboxylic acid bis(2-(2-methylprop-2-oxy)ethyl) ester.

1,2-hydrazinedicarboxylic acid bis(2-methoxyethyl) ester and 1,2-hydrazinedicarboxylic acid bis(2-ethoxyethyl) ester are preferable, and 1,2-hydrazinedicarboxylic acid bis(2-methoxyethyl) ester is particularly preferable.

There is no particular limitation with respect to the oxidizing agent used for this reaction. Preferable specific examples thereof include chlorine, bromine, iodine, sodium hypochlorite, sodium hypobromite, sodium hypoiodite, N-chlorosuccinimide, N-bromosuccinimide, N-iodosuccinimide, hydrogen peroxide, and a hydrogen peroxide-urea complex. Among these, chlorine, bromine, and N-bromosuccinimide are particularly preferable. The amount of oxidizing agent used per mol of the 1,2-hydrazinedicarboxylic acid bis(2-alkoxyethyl) ester compound represented by formula (3) is preferably 1.0 mol to 2.0 mol, more preferably 1.0 mol to 1.5 mol.

A base may be used in this reaction, and there is no particular limitation with respect to the base. Specific preferable examples thereof include: alkali metal salts such as lithium hydroxide, sodium hydroxide, potassium hydroxide, cesium hydroxide, lithium carbonate, sodium carbonate, potassium carbonate, and cesium carbonate; alkaline-earth metal salts such as magnesium hydroxide, calcium hydroxide, barium hydroxide, magnesium carbonate, calcium carbonate, and barium carbonate; and tertiary amines such as trimethylamine, triethylamine, tripropylamine, diisopropylethylamine, tributylamine, tripentylamine, trihexylamine, trioctylamine, triallylamine, pyridine, 2-methylpyridine, 3-methylpyridine, 4-methylpyridine, N-methylmorpholine, N,N-dimethylcyclohexylamine, N,N-dimethylaniline, N-methylimidazole, 1,4-diazabicyclo[2.2.2]octane, and 1,8-diazabicyclo[5.4.0]undec-7-ene. Among these, triethylamine and pyridine are particularly preferable. The amount of base used per mol of the 1,2-hydrazodicarboxylic acid bis(2-alkoxyethyl) ester compound represented by formula (3) is preferably 0.5 mol to 5.0 mol, more preferably 1.0 mol to 3.0 mol.

The reaction solvent is not particularly limited, as long as it does not react with the reagents used for the reaction. Preferable specific examples thereof include hydrocarbon solvents such as n-pentane, n-hexane, cyclohexane, n-heptane, and n-octane; ether solvents such as diethyl ether, diisopropyl ether, tetrahydrofuran, dimethoxyethane, cyclopentyl methyl ether, t-butyl methyl ether, and anisole; aromatic solvents such as benzene, toluene, and xylene; halogenated solvents such as dichloromethane, chloroform, carbon tetrachloride, dichloroethane, and dichloropropane; and aqueous solvents. Among these, tetrahydrofuran, toluene, dichloromethane, and water are particularly preferable. The amount of solvent used per gram of the 1,2-hydrazinedicarboxylic acid bis(2-alkoxyethyl) ester compound represented by formula (3) is preferably 0.5 mL to 50 mL, more preferably 2 mL to 20 mL.

This reaction is performed by mixing, in a reaction solvent, the 1,2-hydrazinedicarboxylic acid bis(2-alkoxyethyl) ester compound represented by formula (3), an oxidizing agent, and as needed, a base. The reaction temperature is preferably 0° C. to 60° C., more preferably about 0° C. to 30° C., since too low a reaction temperature results in a low reaction rate, and too high a reaction temperature results in an increase in the amount of the by-product. The reaction period is preferably 0.5 hour to 24 hours, more preferably about 0.5 hour to 12 hours.

After the reaction, water is added to stop the reaction if a solvent other than water is used. Subsequently, an ordinary method such as extraction, washing, dehumidification, or solvent removal is carried out to give a crude product, which is then purified, for example, by crystallization, recrystallization, or column chromatography, to give an azodicarboxylic acid bis(2-alkoxyethyl) ester compound represented by formula (1).

Since conventional azodicarboxylic acid diesters such as diethyl azodicarboxylate and diisopropyl azodicarboxylate are liquid, purification by distillation must be performed. During distillation, heat is applied, and thus there is a danger of explosion caused by thermal decomposition, for example. In contrast, the azodicarboxylic acid bis(2-alkoxyethyl) ester compound represented by formula (1) is crystalline, and thus can be produced industrially safely without the need of purification by distillation.

In addition, the azodicarboxylic acid bis(2-alkoxyethyl) ester compound represented by formula (1) falls under the category of Type 5 hazardous materials (self-reacting materials) under the Japanese Fire Service Act, and therefore may be dissolved before shipment in an organic solvent at a ratio such that the quality of the compound is not reduced, thereby increasing the safety to about the same level as that of general purpose organic solvents which fall under the category of Type 4 hazardous materials (flammable liquids) under the Japanese Fire Service Act. In this case, examples of organic solvents include ether-based solvents, ketone-based solvents, nitrile-based solvents, aliphatic solvents, aromatic solvents, and halogen-based solvents. Examples of the ether-based solvents include diethyl ether, methyl tertiary butyl ether, isopropyl ether, tetrahydrofuran, dioxane, and cyclopentyl methyl ether, examples of the ketone-based solvents include acetone, methyl ethyl ketone, methyl isobutyl ketone, and cyclohexanone, examples of the nitrile-based solvents include acetonitrile, examples of the aliphatic solvents include hexane, heptane, cyclohexane, and octane, examples of the aromatic solvents include toluene, xylene, benzene, and mesitylene, and examples of the halogen-based solvents include dichloromethane and chloroform. However, examples are not limited to these.

There are cis and trans isomers of the azodicarboxylic acid bis(2-alkoxyethyl) ester compound represented by formula (1) as represented by the following formulae.

[Chem. 9]

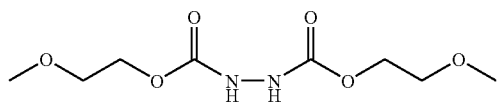

trans

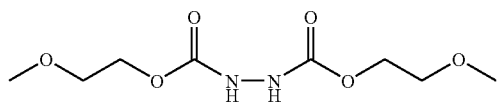

cis

When a Mitsunobu reaction, which causes dehydration condensation, or oxidation reaction is performed using a phosphorus compound and an azodicarboxylic acid bis(2-alkoxyethyl) ester compound represented by formula (1), a 1,2-hydrazinedicarboxylic acid bis(2-alkoxyethyl) ester compound represented by formula (3) is generated as a by-product. This by-product dissolves in an amount of 0.55 g per mL of water (22° C.), and thus can be removed simply by washing the extraction solvent with water. Therefore, the by-product can be removed more easily than in the case of conventional azodicarboxylic acid diesters.

Accordingly, in the case of a Mitsunobu reaction product obtained in this manner, the by-product can be removed simply by washing the extraction solvent with water. Mitsunobu reaction products obtained in this manner may be applied to, for example, medical drugs, physiologically active natural products and the like.

EXAMPLES

The present invention will be described in more detail by way of the following examples, but the invention is by no means limited to these examples.

Example 1

Production of 1,2-hydrazinedicarboxylic acid bis(2-methoxyethyl) ester

[Chem. 10]

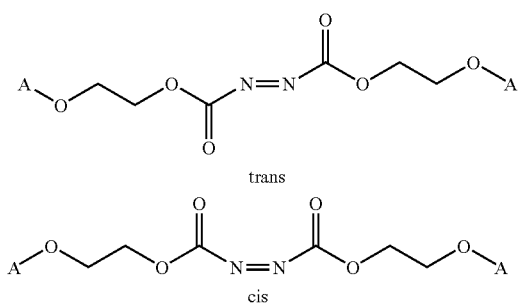

To a solution obtained by adding hydrazine hydrate (15 g, 300 mmol) and 99.5% ethanol (75 ml) to a 500 ml flask, followed by cooling to 6° C., was added dropwise chloroformic acid bis(2-methoxyethyl) ester (41.41 g, 300 mmol) at a temperature of not more than 20° C. Subsequently, chloroformic acid bis(2-methoxyethyl) ester (41.41 g, 300 mmol) and sodium carbonate (31.76 g, 300 mmol) dissolved in water (120 ml) were simultaneously added dropwise at a temperature of not more than 20° C., and the reaction was allowed to proceed for one hour. After the reaction, the reaction solution was concentrated to dryness, and acetone (100 mL) was then added thereto, followed by removal of the solid by filtration. After concentrating the resulting filtrate to dryness, recrystallization was carried out using acetone (75 ml) and toluene (120 mL), to give 1,2-hydrazinedicarboxylic acid bis(2-methoxyethyl) ester as a white crystal (50.91 g, yield: 71.9%).

Mp: 71.3-76.5° C.

IR (KBr): 3258, 1748, 1694, 1518, 1454, 1256, 1244, 1207, 1103, 1105, 1066, 1043, 860 cm$^{-1}$.

$^1$H NMR (400 MHz, CDCl$_3$): δ 7.02 (brs, 2H), 4.27-4.25 (m, 4H), 3.58-3.56 (m, 4H), 3.49 (s, 6H).

$^{13}$C NMR (400 MHz, CDCl$_3$): δ 156.59, 70.40, 64.68, 58.69.

Elemental Analysis
Calculated value: $C_8H_{16}N_2O_6$: C, 40.68; H, 6.83; N, 11.96.
Measured value: C, 40.88; H, 7.49; N, 12.07.

Example 2

Production of 1,2-hydrazinedicarboxylic acid bis(2-methoxyethyl) ester

[Chem. 11]

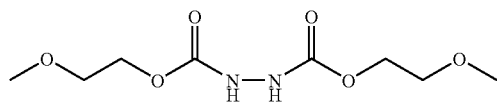

To a solution obtained by adding hydrazine hydrate (200 mg, 4.0 mmol), triethylamine (1.11 ml, 8.0 mmol), and tetrahydrofuran (6 ml) to a 20 ml flask, followed by cooling with an ice bath, was added dropwise chloroformic acid bis(2-methoxyethyl) ester (1.38 g, 12.0 mmol), and the reaction was allowed to proceed for two hours. After the reaction, a crude product obtained by concentrating the reaction solution to dryness was purified by column chromatography (silica gel, ethyl acetate), to give 1,2-hydrazinedicarboxylic acid bis(2-methoxyethyl) ester as a white solid (648 mg, yield: 69%).

$^1$H NMR (400 MHz, CDCl$_3$): δ 7.02 (brs, 2H), 4.27-4.25 (m, 4H), 3.58-3.56 (m, 4H), 3.49 (s, 6H).

Example 3

Production of 1,2-hydrazinedicarboxylic acid bis(2-methoxyethyl) ester

[Chem. 12]

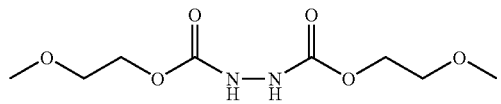

To a solution obtained by adding hydrazine hydrate (200 mg, 4.0 mmol), triethylamine (1.11 ml, 8.0 mmol), and acetonitrile (10 ml) to a 30 ml flask, followed by cooling with an ice bath, was added dropwise chloroformic acid bis(2-methoxyethyl) ester (1.38 g, 12.0 mmol), and the reaction was allowed to proceed for one hour. After the reaction, a crude product obtained by concentrating the reaction solution to dryness was purified by column chromatography (silica gel, ethyl acetate), to give 1,2-hydrazinedicarboxylic acid bis(2-methoxyethyl) ester as a white solid (635 mg, yield: 67%).

$^1$H NMR (400 MHz, CDCl$_3$): δ 7.02 (brs, 2H), 4.27-4.25 (m, 4H), 3.58-3.56 (m, 4H), 3.49 (s, 6H).

Example 4

Production of 1,2-hydrazinedicarboxylic acid bis(2-methoxyethyl) ester

[Chem. 13]

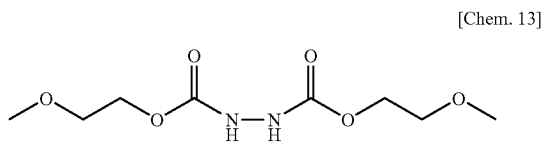

To a solution obtained by adding hydrazine hydrate (200.5 mg, 4.0 mmol), sodium carbonate (424 mg, 4.0 mmol), and tetrahydrofuran (6 ml) to a 20 ml flask, followed by cooling with an ice bath, was added dropwise chloroformic acid bis(2-methoxyethyl) ester (1.38 g, 12.0 mmol), and the reaction was allowed to proceed for one hour. After the reaction, a crude product obtained by concentrating the reaction solution to dryness was purified by column chromatography (silica gel, ethyl acetate), to give 1,2-hydrazinedicarboxylic acid bis(2-methoxyethyl) ester as a white solid (732 mg, yield: 78%).

$^1$H NMR (400 MHz, CDCl$_3$): δ7.02 (brs, 2H), 4.27-4.25 (m, 4H), 3.58-3.56 (m, 4H), 3.49 (s, 6H).

Example 5

Production of 1,2-hydrazinedicarboxylic acid bis(2-methoxyethyl) ester

[Chem. 14]

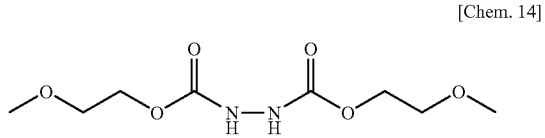

To a solution obtained by adding hydrazine hydrate (200 mg, 4.0 mmol), potassium carbonate (553 mg, 4.0 mmol), and acetonitrile (10 ml) to a 30 ml flask, followed by cooling with an ice bath, was added dropwise chloroformic acid bis(2-methoxyethyl) ester (1.38 g, 12.0 mmol), and the reaction was allowed to proceed for one hour. After the reaction, a crude product obtained by concentrating the reaction solution to dryness was purified by column chromatography (silica gel, ethyl acetate), to give 1,2-hydrazinedicarboxylic acid bis(2-methoxyethyl) ester as a white solid (708 mg, yield: 75%).

$^1$H NMR (400 MHz, CDCl$_3$): δ 7.02 (brs, 2H), 4.27-4.25 (m, 4H), 3.58-3.56 (m, 4H), 3.49 (s, 6H).

Example 6

Production of azodicarboxylic acid bis(2-methoxyethyl) ester

[Chem. 15]

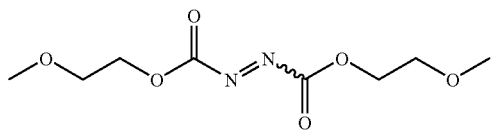

1,2-hydrazinedicarboxylic acid bis(2-methoxyethyl) ester (45 g, 191 mmol), pyridine (15.09 g, 191 mmol), and toluene (450 ml) were added to a 1000 ml flask, and N-bromosuccinimide (37.31 g, 210 mmol) was slowly added thereto at 20° C., followed by allowing the reaction to proceed for two hours. After the reaction, the solution was washed with water (180 mL,×2), and dehumidified with anhydrous magnesium sulfate, followed by concentration to dryness. The resulting solid was recrystallized with toluene (67.5 ml) and hexane (337.5 ml), to give azodicarboxylic acid bis(2-methoxyethyl) ester as a pale yellow crystal (39.26 g, yield: 88.0%).

Mp: 39.9-40.4° C.

IR (KBr): 2940, 2899, 1782, 1450, 1371, 1281, 1240, 1200, 1136, 1094, 1036, 1016, 962, 866, 810, 527 cm$^{-1}$.

$^1$H NMR (400 MHz, CDCl$_3$): δ 4.51-4.49 (m, 4H), 3.66-3.63 (m, 4H), 3.32 (s, 6H).

$^{13}$C NMR (400 MHz, CDCl$_3$): δ 156.59, 70.40, 64.68, 58.69.

Elemental Analysis

Calculated value: C$_8$H$_{14}$N$_2$O$_6$: C, 41.03; H, 6.03; N, 11.96.
Measured value: C, 41.09; H, 6.65; N, 11.98.

Example 7

Production of azodicarboxylic acid bis(2-methoxyethyl) ester

[Chem. 16]

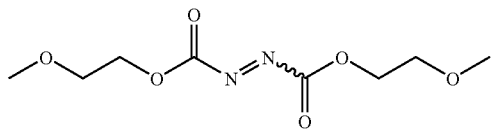

To a solution obtained by adding 1,2-hydrazinedicarboxylic acid bis(2-methoxyethyl) ester (200 mg, 0.85 mmol) and toluene (2 mL) to a 10 mL flask, followed by cooling with an ice bath, was added dropwise a 5% sodium hypochlorite solution (1.39 g, 0.85 mmol), and the reaction was allowed to proceed for one hour. After the reaction, the solution was washed with water (1 mL,×2), and dehumidified with anhydrous magnesium sulfate, followed by concentration to dryness. The resulting solid was recrystallized with toluene (1 mL) and hexane (5 mL), to give azodicarboxylic acid bis(2-methoxyethyl) ester as a pale yellow crystal (73 mg, yield: 37%).

$^1$H NMR (400 MHz, CDCl$_3$): δ 4.51-4.49 (m, 4H), 3.66-3.63 (m, 4H), 3.32 (s, 6H).

Example 8

Production of azodicarboxylic acid bis(2-methoxyethyl) ester

[Chem. 17]

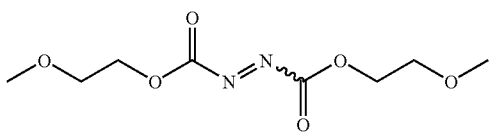

To a solution obtained by adding 1,2-hydrazinedicarboxylic acid bis(2-methoxyethyl) ester (1 g, 4.23 mmol), pyridine (0.34 g, 4.23 mmol), and toluene (10 ml) to a 30 ml flask, followed by cooling with an ice bath, chlorine gas was blown for 30 minutes. After the reaction, the solution was washed with water (1 mL,×2), and dehumidified with anhydrous magnesium sulfate, followed by concentration to dryness. The solid was recrystallized with toluene (1.5 mL) and hexane (7.5 mL), to give azodicarboxylic acid bis(2-methoxyethyl) ester as a pale yellow crystal (0.59 g, yield: 60%).

$^1$H NMR (400 MHz, CDCl$_3$): δ 4.51-4.49 (m, 4H), 3.66-3.63 (m, 4H), 3.32 (s, 6H).

Example 9

Production of (4S,2R)-4-(4-nitrobenzoyloxy)pentane-2-ol: Utilization for Mitsunobu reaction

[Chem. 18]

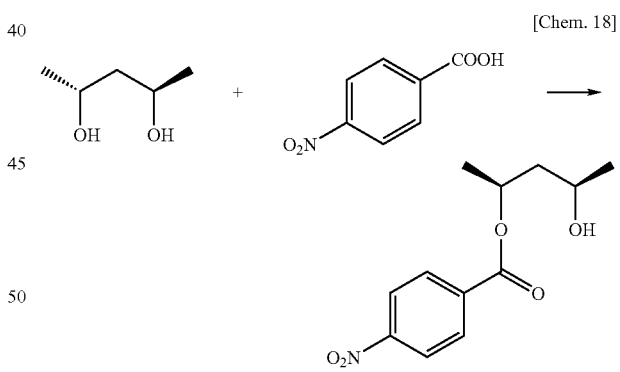

After triphenylphosphine (565 mg, 2.16 mmol), (2R,4R)-2,4-pentanediol (226 mg, 2.16 mmol), and THF (6 ml) were added to a 50 mL flask, azodicarboxylic acid bis(2-methoxyethyl) ester (505 mg, 2.16 mmol) dissolved in THF (6 mL) was added dropwise thereto at 20° C. Subsequently, 4-nitrobenzoic acid (300 mg, 1.80 mmol) dissolved in THF (6 mL) was added dropwise thereto at 20° C., and the reaction was allowed to proceed for one hour. Water (0.5 ml) was added, and concentration was carried out. Then, water (10 ml) was added to the solution, and extraction was carried out using diethyl ether (10 mL,×2). Then, the organic layer was washed with water (10 ml) and saturated salt water (10 ml), and dehumidified with anhydrous magnesium sulfate. Subsequently, a crude product obtained by concentration was purified by column chromatography (silica gel, 40% ethyl acetate-hexane solution) to give (4S,2R)-4-(4-nitrobenzoyloxy)pentane-2-ol as a pale yellow solid substance (358 mg, yield: 79%/4-nitrobenzoic acid).

Mp: 48.4-50.7° C.

Specific rotation: $[\alpha]_D^{20}$=+9.86 (c 1.23, MeOH).

IR (KBr): 3416, 2972, 1722, 1607, 1530, 1350, 1285, 1103, 874, 719 cm$^{-1}$.

$^1$H NMR (600 MHz, CDCl$_3$): δ 8.26 (d, J=8.9 Hz, 2H), 8.18 (d, J=8.9 Hz, 2H), 5.34 (m, 1H), 3.95 (m, 1H), 2.01 (m, 1H), 1.72 (m, 1H), 1.55 (brd, 1H), 1.41 (d, J=6.2 Hz, 3H), 1.24 (d, J=6.2 Hz, 3H).

$^{13}$C NMR (100 MHz, CDCl$_3$): δ 164.15, 150.30, 135.89, 130.50, 123.34, 71.10, 65.18, 44.93, 23.81, 20.04.

Elemental Analysis

Calculated value: C$_{12}$H$_{15}$NO$_5$: C, 56.91; H, 5.97; N, 5.53.

Measured value: C, 56.82; H, 6.27; N, 5.60.

Comparative Example 1

Comparative Example for Example 9 (Using Azodicarboxylic Acid Diisopropyl Ester)

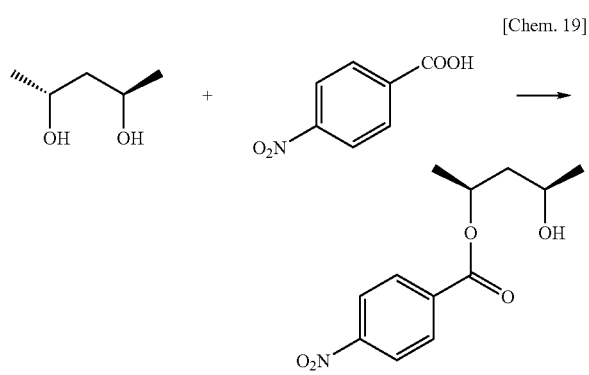

[Chem. 19]

After triphenylphosphine (566 mg, 2.16 mmol), (2R,4R)-2,4-pentanediol (225 mg, 2.16 mmol), and THF (6 ml) were added to a 50 mL flask, a 40% azodicarboxylic acid diisopropyl ester-toluene solution (1.13 mL, 2.16 mmol) dissolved in THF (6 mL) was added dropwise thereto at 20° C. Subsequently, 4-nitrobenzoic acid (300 mg, 1.80 mmol) dissolved in THF (6 mL) was added dropwise thereto at 20° C., and the reaction was allowed to proceed for one hour. Water (0.5 ml) was added, and concentration was carried out. Then, water (10 ml) was added to the solution, and extraction was carried out using diethyl ether (10 mL,×2). Then, the organic layer was washed with water (10 ml) and saturated salt water (10 ml), and dehumidified with anhydrous magnesium sulfate. Subsequently, a crude product obtained by concentration was purified by column chromatography (silica gel, 40% ethyl acetate-hexane solution) to give (4S,2R)-4-benzoyloxypentane-2-ol containing 1,2-hydrazinedicarboxylic acid diisopropyl ester as 593 mg of a pale yellow solid substance. Measurement of $^1$H-NMR showed that 379 mg of (4S,2R)-4-(4-nitrobenzoyloxy)pentane-2-ol (yield: 83%/4-nitrobenzoic acid), and 213 mg of 1,2-hydrazinedicarboxylic acid diisopropyl ester were contained.

Example 10

Production of (4S,2R)-4-(4-nitrobenzoyloxy)pentane-2-ol: utilization for Mitsunobu reaction

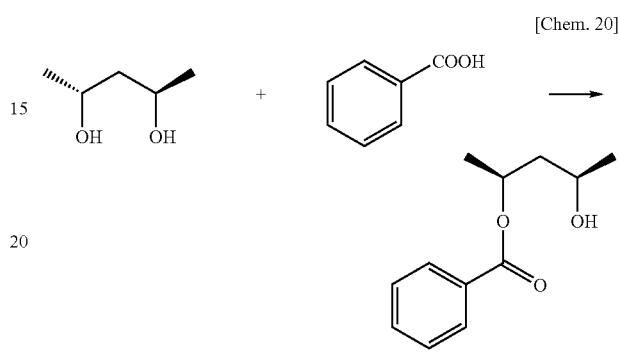

[Chem. 20]

After benzoic acid (300 mg, 2.46 mmol), triphenylphosphine (775 mg, 2.95 mmol), (2R,4R)-2,4-pentanediol (308 mg, 2.95 mmol), and THF (12 ml) were added to a 50 ml flask, azodicarboxylic acid bis(2-methoxyethyl) ester (691.1 mg, 2.95 mmol) dissolved in THF (6 mL) was added dropwise thereto at 20° C., and the reaction was allowed to proceed for one hour. Water (0.5 ml) was added, and concentration was carried out. Then, water (10 ml) was added to the solution, and extraction was carried out using diethyl ether (10 mL,×2). Then, the organic layer was washed with water (10 ml) and saturated salt water (10 ml), and dehumidified with anhydrous magnesium sulfate. Subsequently, a crude product obtained by concentration was purified by column chromatography (silica gel, 40% ethyl acetate-hexane solution) to give (4S,2R)-4-benzoyloxypentane-2-ol as a colorless oily substance (379 mg, yield: 74%/benzoic acid).

Specific rotation: $[\alpha]_D^{20}$=+33.1 (c 1.12, MeOH).

IR (KCl, neat): 3416, 2972, 2932, 1715, 1450, 1315, 1279, 1111, 1099, 1070, 1026, 712 cm$^{-1}$.

$^1$H NMR (600 MHz, CDCl$_3$): δ 7.97 (d, J=7.6 Hz, 2H), 7.45 (d, J=7.6 Hz, 1H), 7.34 (d, J=7.6 Hz, 2H), 5.28 (m, 1H), 3.96 (m, 1H), 2.00 (m, 1H), 1.70 (m, 1H), 1.65 (brs, 1H), 1.38 (d, J=6.2 Hz, 3H), 1.23 (d, J=6.2 Hz, 3H).

$^{13}$C NMR (100 MHz, CDCl$_3$): δ 166.11, 132.79, 130.43, 129.39, 128.23, 69.95, 65.29, 45.17, 23.61, 20.25.

Elemental Analysis

Calculated value: C$_{12}$H$_{16}$O$_3$: C, 69.21; H, 7.74.

Measured value: C, 68.84; H, 7.63.

Comparative Example 2

Comparative Example for Example 10 (Using Azodicarboxylic Acid Diisopropyl Ester)

After benzoic acid (300.6 mg, 2.46 mmol), triphenylphosphine (776.2 mg, 2.95 mmol), (2R,4R)-2,4-pentanediol (309.1 mg, 2.95 mmol), and THF (12 mL) were added to a 50 ml flask, a 40% azodicarboxylic acid diisopropyl ester-toluene solution (1.55 ml, 2.95 mmol) dissolved in THF (6 ml) was added dropwise thereto at 20° C., and the reaction was allowed to proceed for ix hours. Water (0.5 ml) was added, and concentration was carried out. Then, water (10 ml) was added to the solution, and extraction was carried out using diethyl ether (10 ml,×2). Then, the organic layer was washed with water (10 ml) and saturated salt water (10 ml), and dehumidified with anhydrous magnesium sulfate. Subsequently, a crude product obtained by concentration was purified by column chromatography (silica gel, 40% ethyl acetate-hexane solution) to give (4S,2R)-4-benzoyloxypentane-2-ol containing 1,2-hydrazinedicarboxylic acid diisopropyl ester as 525.3 mg of a colorless oily substance. Measurement of $^1$H-NMR showed that 380 mg of (4S,2R)-4-benzoyloxypentane-2-ol (yield: 74%/benzoic acid), and 146 mg of 1,2-hydrazinedicarboxylic acid diisopropyl ester were contained.

Example 11

Production of (4S,2R)-4-(4-methoxyphenoxy)pentane-2-ol: Utilization for Mitsunobu reaction

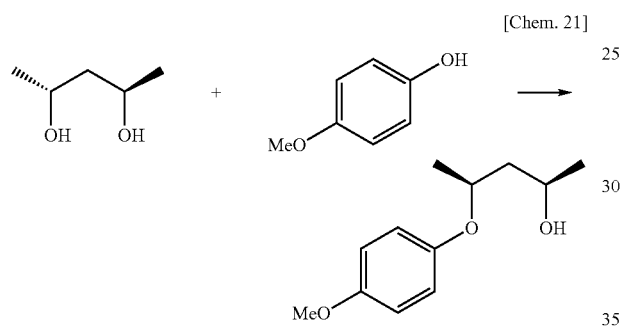

[Chem. 21]

After 4-methoxyphenol (300 mg, 2.41 mmol), triphenylphosphine (761 mg, 2.89 mmol), (2R,4R)-2,4-pentanediol (302 mg, 2.89 mmol), and THF (12 mL) were added to a 50 ml flask, azodicarboxylic acid bis(2-methoxyethyl) ester (680 mg, 2.89 mmol) dissolved in THF (6 ml) was added dropwise thereto at 20° C., and the reaction was allowed to proceed for 14 hours. Water (0.5 ml) was added, and concentration was carried out. Then, water (10 ml) was added to the solution, and extraction was carried out using diethyl ether (10 mL,×2). Then, the organic layer was washed with water (10 ml) and saturated salt water (10 ml), and dehumidified with anhydrous magnesium sulfate. Subsequently, a crude product obtained by concentration was purified by column chromatography (silica gel, 30% ethyl acetate-hexane solution) to give (4S,2R)-4-(4-methoxyphenoxy)pentane-2-ol as a colorless oily substance (418 mg, yield: 82%/4-methoxyphenol).

Specific rotation: $[\alpha]_D^{20}$=+6.92 (c 1.09, MeOH).

IR (KCl, neat): 3430, 2840, 1510, 1240, 1040, 830 cm$^{-1}$.

$^1$H NMR (600 MHz, CDCl$_3$): δ 6.87 (d, J=9.3 Hz, 2H), 6.80 (d, J=6.3 Hz, 2H), 4.44 (m, 1H), 4.06 (m, 1H), 3.75 (s, 3H), 2.70 (brs, 1H), 1.89 (m, 1H), 1.66 (ddd, J=14.4, 4.2, 2.9 Hz, 1H), 1.24 (d, J=5.9, Hz, 3H), 1.20 (d, J=6.4 Hz, 3H).

$^{13}$C NMR (100 MHz, CDCl$_3$): δ 154.13, 150.94, 117.81, 114.52, 74.90, 66.67, 55.47, 45.32, 23.55, 19.77.

Mass spectrometry analysis: MS (M$^+$), m/z (%) 210 (12), 186 (9), 162 (20), 150 (10), 124 (100), 109 (30), 108 (10).

High-Resolution Mass Spectrometry Analysis

Calculated value: C$_{12}$H$_{18}$O$_3$, 210.1256

Measured value: 210.1242.

Comparative Example 3

Comparative Example for Example 11 (Using Azodicarboxylic Acid Diisopropyl Ester)

After 4-methoxyphenol (300 mg, 2.41 mmol), triphenylphosphine (762 mg, 2.89 mmol), (2R,4R)-2,4-pentanediol (303 mg, 2.89 mmol), and THF (12 ml) were added to a 50 ml flask, a 40% azodicarboxylic acid diisopropyl ester-toluene solution (1.53 mL, 2.89 mmol) dissolved in THF (6 ml) was added dropwise thereto at 20° C., and the reaction was allowed to proceed for 17 hours. Water (0.5 ml) was added, and concentration was carried out. Then, water (10 ml) was added to the solution, and extraction was carried out using diethyl ether (10 ml,×2). Then, the organic layer was washed with water (10 ml) and saturated salt water (10 ml), and dehumidified with anhydrous magnesium sulfate. Subsequently, a crude product obtained by concentration was purified by column chromatography (silica gel, 30% ethyl acetate-hexane solution) to give (4S,2R)-4-(4-methoxyphenoxy)pentane-2-ol containing 1,2-hydrazinedicarboxylic acid diisopropyl ester as 543 mg of a colorless oily substance. Measurement of $^1$H-NMR showed that 420 mg of (4S,2R)-4-benzoyloxypentane-2-ol (yield: 83%/4-methoxyphenol), and 123 mg of 1,2-hydrazinedicarboxylic acid diisopropyl ester were contained.

Example 12

Production of Benzoic acid 4-((1S,3R)-3-hydroxy-1-methylbutoxy) ester: Utilization for Mitsunobu reaction

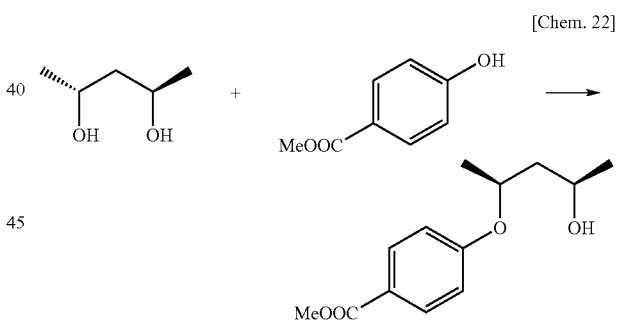

[Chem. 22]

After methyl 4-hydroxybenzoate (300 mg, 1.97 mmol), triphenylphosphine (620.5 mg, 2.36 mmol), (2R,4R)-2,4-pentanediol (247 mg, 2.36 mmol), and THF (12 ml) were added to a 50 ml flask, azodicarboxylic acid bis(2-methoxyethyl) ester (554 mg, 2.36 mmol) dissolved in THF (6 mL) was added dropwise thereto at 20° C., and the reaction was allowed to proceed for five hours. Water (0.5 ml) was added, and concentration was carried out. Then, water (10 ml) was added to the solution, and extraction was carried out using diethyl ether (10 ml,×2). Then, the organic layer was washed with water (10 ml) and saturated salt water (10 ml), and dehumidified with anhydrous magnesium sulfate. Subsequently, a crude product obtained by concentration was purified by column chromatography (silica gel, 40% ethyl acetate-hexane solution) to give benzoic acid 4-((1S,3R)-3-hydroxy-1-methylbutoxy) ester as a colorless oily substance (389 mg, yield: 83%/methyl 4-hydroxybenzoate).

Specific rotation: $[\alpha]_D^{20} = +24.6$ (c 0.65, MeOH).

IR (KCl, neat): 3437, 2972, 1714, 1605, 1508, 1435, 1283, 1254, 1171, 1113, 849, 772 cm$^{-1}$.

$^1$H NMR (600 MHz, CDCl$_3$): δ 7.96 (dm, J=8.9 Hz, 2H), 6.91 (dm, J=8.9 Hz, 2H), 4.68 (m, 1H), 4.01 (m, 1H), 3.86 (s, 3H), 1.96 (ddd, J=14.4, 8.8, 7.6 Hz, 1H), 1.69 (ddd, J=14.4, 6.4, 3.4 Hz, 1H), 1.58 (brs, 1H), 1.33 (d, J=5.9, Hz, 3H), 1.22 (d, J=6.4 Hz, 3H).

$^{13}$C NMR (100 MHz, CDCl$_3$): δ 166.79, 161.25, 131.58, 122.45, 115.14, 72.82, 66.08, 51.80, 45.17, 23.82, 19.61.

High-Resolution Mass Spectrometry Analysis

Calculated value: $C_{13}H_{18}O_4$, 238.1205.

Measured value: 238.1181.

Comparative Example 4

Comparative Example for Example 12 (Using Azodicarboxylic Acid Diisopropyl Ester)

After methyl 4-hydroxybenzoate (300 mg, 1.97 mmol), triphenylphosphine (621 mg, 2.36 mmol), (2R,4R)-2,4-pentanediol (247 mg, 2.36 mmol), and THF (12 ml) were added to a 50 ml flask, a 40% azodicarboxylic acid diisopropyl ester-toluene solution (1.25 ml, 2.36 mmol) dissolved in THF (6 ml) was added dropwise thereto at 20° C., and the reaction was allowed to proceed for 17 hours. Water (0.5 ml) was added, and concentration was carried out. Then, water (10 ml) was added to the solution, and extraction was carried out using diethyl ether (10 ml,×2). Then, the organic layer was washed with water (10 ml) and saturated salt water (10 ml), and dehumidified with anhydrous magnesium sulfate. Subsequently, a crude product obtained by concentration was purified by column chromatography (silica gel, 40% ethyl acetate-hexane solution) to give benzoic acid 4-((1S,3R)-3-hydroxy-1-methylbutoxy) ester containing 1,2-hydrazinedicarboxylic acid diisopropyl ester as 643 mg of a colorless oily substance. Measurement of $^1$H-NMR showed that 426 mg of benzoic acid 4-((1S,3R)-3-hydroxy-1-methylbutoxy) ester (yield: 91%/methyl 4-hydroxybenzoate), and 217 mg of 1,2-hydrazinedicarboxylic acid diisopropyl ester were contained.

Example 13

Production of (4S,2R)-4-phenoxypentane-2-ol: utilization for Mitsunobu reaction

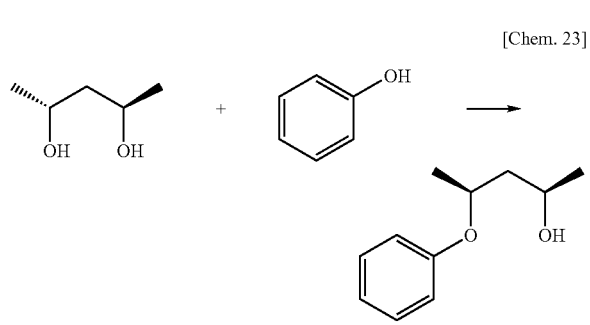

[Chem. 23]

After phenol (300 mg, 3.19 mmol), triphenylphosphine (1008 mg, 3.83 mmol), (2R,4R)-2,4-pentanediol (399 mg, 3.83 mmol), and THF (12 ml) were added to a 50 ml flask, azodicarboxylic acid bis(2-methoxyethyl) ester (896 mg, 3.83 mmol) dissolved in THF (6 mL) was added dropwise thereto at 20° C., and the reaction was allowed to proceed for 21 hours. Water (0.5 ml) was added, and concentration was carried out. Then, water (10 ml) was added to the solution, and extraction was carried out using diethyl ether (10 ml,×2). Then, the organic layer was washed with water (10 ml) and saturated salt water (10 ml), and dehumidified with anhydrous magnesium sulfate. Subsequently, a crude product obtained by concentration was purified by column chromatography (silica gel, 40% ethyl acetate-hexane solution) to give (4S,2R)-4-phenoxypentane-2-ol as a colorless oily substance (481 mg, yield: 84%/phenol).

Specific rotation: $[\alpha]_D^{20} = +14.97$ (c 1.00, MeOH).

IR (KCl, neat): 3400, 2940, 1600, 1500, 1380, 1250, 1120, 760, 700 cm$^{-1}$.

$^1$H NMR (600 MHz, CDCl$_3$): δ 7.28-7.21 (m, 2H), 6.95-6.90 (m, 3H), 4.58 (m, 1H), 4.04 (m, 1H), 2.15 (brs, 1H), 1.93 (ddd, J=14.2, 8.8, 5.9 Hz, 1H), 1.68 (ddd, J=14.2, 4.3, 3.0 Hz, 1H), 1.29 (d, J=6.0, Hz, 3H), 1.23 (d, J=6.3 Hz, 3H).

$^{13}$C NMR (100 MHz, CDCl$_3$): δ 157.08, 129.40, 120.97, 116.00, 73.25, 66.46, 45.30, 23.55, 19.72.

Elemental Analysis

Calculated value: $C_{11}H_6O_2$: C, 73.30; H, 8.95.

Measured value: C, 72.93; H, 8.67.

Comparative Example 5

Comparative Example for Example 13 (Using Azodicarboxylic Acid Diisopropyl Ester)

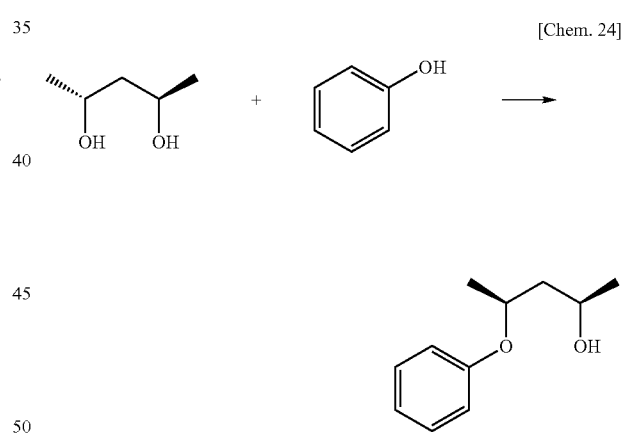

[Chem. 24]

After phenol (300 mg, 3.19 mmol), triphenylphosphine (1006 mg, 3.83 mmol), (2R,4R)-2,4-pentanediol (399 mg, 3.83 mmol), and THF (12 ml) were added to a 50 ml flask, a 40% azodicarboxylic acid diisopropyl ester-toluene solution (2.01 ml, 3.83 mmol) dissolved in THF (6 ml) was added dropwise thereto at 20° C., and the reaction was allowed to proceed for 21 hours. Water (0.5 ml) was added, and concentration was carried out. Then, water (10 ml) was added to the solution, and extraction was carried out using diethyl ether (10 ml,×2). Then, the organic layer was washed with water (10 ml) and saturated salt water (10 ml), and dehumidified with anhydrous magnesium sulfate. Subsequently, a crude product obtained by concentration was purified by column chromatography (silica gel, 40% ethyl acetate-hexane solution) to give (4S,2R)-4-phenoxypentane-2-ol as a colorless oily substance (461 mg, yield: 80%/phenol).

Example 14

Production of (R)-2-benzoyloxyoctane: utilization for Mitsunobu reaction

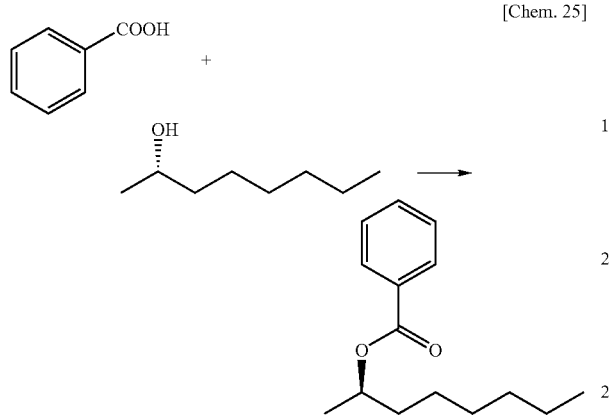

[Chem. 25]

After (S)-2-octanol (300 mg, 2.30 mmol), triphenylphosphine (725 mg, 2.76 mmol), benzoic acid (338 mg, 2.76 mmol), and THF (12 ml) were added to a 50 ml flask, azodicarboxylic acid bis(2-methoxyethyl) ester (649 mg, 2.76 mmol) dissolved in THF (6 ml) was added dropwise thereto at 20° C., and the reaction was allowed to proceed for two hours. Water (0.5 mL) was added, and concentration was carried out. Then, water (10 ml) was added to the solution, and extraction was carried out using diethyl ether (10 ml,×2). Then, the organic layer was washed with water (10 mL) and saturated salt water (10 ml), and dehumidified with anhydrous magnesium sulfate. Subsequently, a crude product obtained by concentration was purified by column chromatography (silica gel, 10% ethyl acetate-hexane solution) to give (R)-2-benzoyloxyoctane as a colorless liquid substance (490 mg, yield: 91%/(S)-2-octanol).

Specific rotation: $[\alpha]_D^{20} = -40.6$ (c 1.06, MeOH)

IR (KCl, neat): 2930, 2859, 1742, 1450, 1314, 1275, 1109, 1069, 1026, 712 cm$^{-1}$.

$^1$H NMR (600 MHz, CDCl$_3$): δ 7.97 (d, J=7.6 Hz, 2H), 7.47 (t, J=7.6 Hz, 1H), 7.36 (t, J=7.6 Hz, 2H), 5.08 (m, 1H), 1.66 (m, 1H), 1.53 (m, 1H), 1.35-1.18 (m, 11H), 0.80 (t, J=6.9 Hz, 3H).

$^{13}$C NMR (100 MHz, CDCl$_3$): δ 163.96, 150.18, 136.06, 130.36, 120.19, 72.83, 35.71, 31.49, 28.91, 25.17, 22.35, 19.68, 13.79.

Comparative Example 6

Comparative Example for Example 14 (Using Azodicarboxylic Acid Diisopropyl Ester)

After (S)-2-octanol (300 mg, 2.30 mmol), triphenylphosphine (728 mg, 2.76 mmol), benzoic acid (338 mg, 2.76 mmol), and THF (12 ml) were added to a 50 ml flask, a 40% azodicarboxylic acid diisopropyl ester-toluene solution (1.45 ml, 2.76 mmol) dissolved in THF (6 ml) was added dropwise thereto at 20° C., and the reaction was allowed to proceed for two hours. Water (0.5 mL) was added, and concentration was carried out. Then, water (10 ml) was added to the solution, and extraction was carried out using diethyl ether (10 ml,×2). Then, the organic layer was washed with water (10 ml) and saturated salt water (10 ml), and dehumidified with anhydrous magnesium sulfate. Subsequently, a crude product obtained by concentration was purified by column chromatography (silica gel, 10% ethyl acetate-hexane solution) to give (R)-2-benzoyloxyoctane as a colorless liquid substance (503 mg, yield: 93%/(S)-2-octanol).

$^1$H NMR (600 MHz, CDCl$_3$): δ 7.97 (d, J=7.6 Hz, 2H), 7.47 (t, J=7.6 Hz, 1H), 7.36 (t, J=7.6 Hz, 2H), 5.08 (m, 1H), 1.66 (m, 1H), 1.53 (m, 1H), 1.35-1.18 (m, 11H), 0.80 (t, J=6.9 Hz, 3H).

Example 15

Production of 2-phenethyl isoindole-1,3-dione: utilization for Mitsunobu reaction

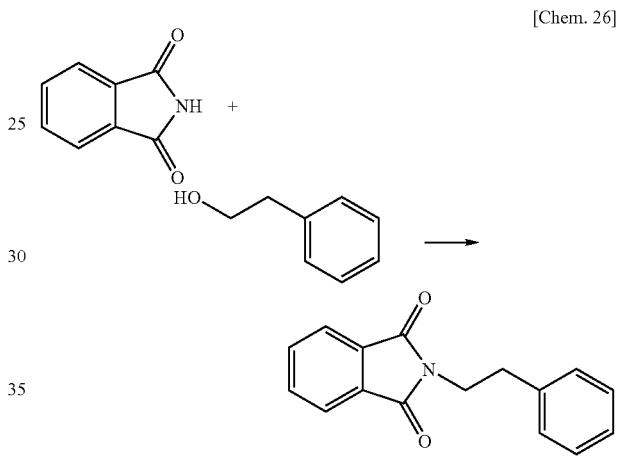

[Chem. 26]

After 2-phenylethyl alcohol (300 mg, 2.46 mmol), triphenylphosphine (775 mg, 2.95 mmol), phthalimide (434 mg, 2.95 mmol), and THF (12 ml) were added to a 50 ml flask, azodicarboxylic acid bis(2-methoxyethyl) ester (697 mg, 2.95 mmol) dissolved in THF (6 ml) was added dropwise thereto at 20° C., and the reaction was allowed to proceed for 2.5 hours. Water (0.5 mL) was added, and concentration was carried out. Then, water (10 ml) was added to the solution, and extraction was carried out using ethyl acetate (10 ml,×2). Then, the organic layer was washed with water (10 mL) and saturated salt water (10 ml), and dehumidified with anhydrous magnesium sulfate. Subsequently, a crude product obtained by concentration was purified by column chromatography (silica gel, 30% ethyl acetate-hexane solution) to give 2-phenethyl isoindole-1,3-dione as a white solid substance (579 mg, yield: 94%/2-phenylethyl alcohol).

Mp: 124.4-125.7° C.

IR (KBr): 2396, 1709, 1429, 1396, 1360, 1101, 1069, 870, 756, 710, 530 cm$^{-1}$.

$^1$H NMR (600 MHz, CDCl$_3$): δ 7.81 (m, 2H), 7.69 (m, 2H), 7.28-7.18 (m, 5H), 3.91 (t, J=7.6 Hz, 2H), 2.97 (t, J=7.6 Hz, 2H).

$^{13}$C NMR (100 MHz, CDCl$_3$): δ 168.11, 137.96, 133.85, 132.02, 128.80, 128.50, 126.59, 123.17, 39.24, 34.60.

Elemental Analysis

Calculated value: $C_{16}H_{13}NO_2$: C, 76.48; H, 5.21; N, 5.57.

Measured value: C, 75.27; H, 5.59; N, 5.84.

Example 16

Production of 4,N-dimethyl-N-(1-methylheptyl)benzenesulfonamide: utilization for Mitsunobu reaction

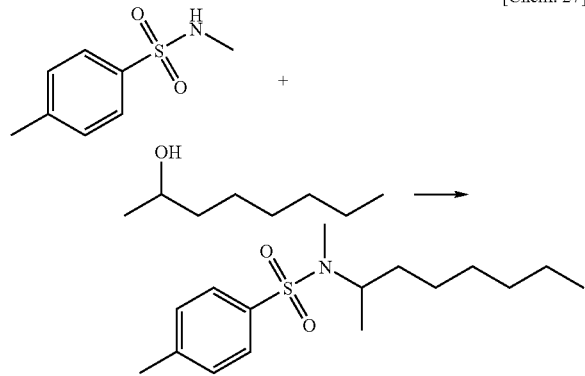

[Chem. 27]

After (racemic)-2-octanol (300 mg, 2.30 mmol), triphenylphosphine (727 mg, 2.76 mmol), N-methyl-p-toluenesulfonamide (514 mg, 2.76 mmol), and THF (12 ml) were added to a 50 ml flask, azodicarboxylic acid bis(2-methoxyethyl) ester (648 mg, 2.76 mmol) dissolved in THF (6 ml) was added dropwise thereto at 20° C., and the reaction was allowed to proceed for 21 hours. Subsequently, a crude product obtained by concentration was purified by column chromatography (silica gel, 10% ethyl acetate-hexane solution) to give 4,N-dimethyl-N-(1-methylheptyl)benzenesulfonamide as a white solid substance (223 mg, yield: 33%/(racemic)-2-octanol).

$^1$H NMR (600 MHz, CDCl$_3$): δ 7.66 (d, J=8.2 Hz, 2H), 7.266 (d, J=8.2 Hz, 2H), 3.96 (m, 1H), 2.64 (s, 3H), 2.39 (s, 3H), 1.37-1.16 (m, 10H), 0.95-0.83 (m, 6H).

$^{13}$C NMR (100 MHz, CDCl$_3$): δ 142.80, 137.29, 129.50, 127.01, 52.75, 34.26, 31.67, 28.95, 27.21, 26.33, 22.53, 21.44, 17.29, 14.05.

IR (KCl, neat): 2955, 2928, 2857, 1597, 1460, 1383, 1339, 1153, 1090, 939, 816, 731, 712, 694, 654, 646, 567, 552 cm$^{-1}$.

Elemental Analysis

Calculated value: C$_{16}$H$_{27}$NO$_2$S: C, 64.60; H, 9.15; N, 4.71; S, 10.78.

Measured value: C, 64.41; H, 9.00; N, 4.83; S, 11.08.

Example 17

Production of acetic acid (1-methyl-1H-tetrazole-5-ylsulfanyl)methyl ester: utilization for Mitsunobu reaction

[Chem. 28]

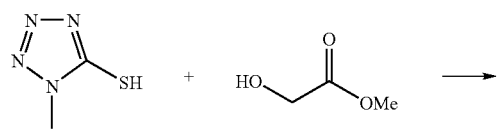

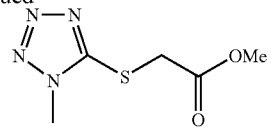

After glycolic acid methyl ester (300 mg, 3.33 mmol), triphenylphosphine (1052 mg, 4.00 mmol), 1-methyl-5-mercapto-1H-tetrazole (465 mg, 4.00 mmol), and THF (12 ml) were added to a 50 ml flask, azodicarboxylic acid bis(2-methoxyethyl) ester (937 mg, 4.00 mmol) dissolved in THF (6 ml) was added dropwise thereto at 20° C., and the reaction was allowed to proceed for two hours. Water (0.5 mL) was added, and concentration was carried out. Then, water (10 ml) was added to the solution, and extraction was carried out using ethyl acetate (10 ml,×2). Then, the organic layer was washed with water (10 mL) and saturated salt water (10 ml), and dehumidified with anhydrous magnesiumسulfate. Subsequently, a crude product obtained by concentration was purified by column chromatography (silica gel, 70% ethyl acetate-hexane solution) to give acetic acid (1-methyl-1H-tetrazole-5-ylsulfanyl)methyl ester as a colorless oily substance (549 mg, yield: 88%/glycolic acid methyl ester).

IR (KCl, neat): 2959, 1755, 1506, 1441, 1358, 1227, 1200, 1148, 1032, 999, 812, 721, 677, 579 cm$^{-1}$.

$^1$H NMR (600 MHz, CDCl$_3$): δ 4.14 (s, 2H), 3.96 (s, 3H), 3.76 (s, 3H).

$^{13}$C NMR (100 MHz, CDCl$_3$): δ 167.82, 152.80, 53.08, 34.77, 33.48.

Elemental Analysis

Calculated value: C$_5$H$_8$N$_4$O$_2$S: C, 31.91; H, 4.28; N, 29.77; S, 17.04.

Measured value: C, 32.02; H, 4.63; N, 30.08; S, 16.44.

Comparative Example 7

Comparative Example for Example 17 (Using Azodicarboxylic Acid Diisopropyl Ester)

After glycolic acid methyl ester (300 mg, 3.33 mmol), triphenylphosphine (1050 mg, 4.00 mmol), 1-methyl-5-mercapto-1H-tetrazole (465 mg, 4.00 mmol), and THF (12 ml) were added to a 50 ml flask, a 40% azodicarboxylic acid diisopropyl ester-toluene solution (2.10 ml, 4.00 mmol) dissolved in THF (6 ml) was added dropwise thereto at 20° C., and the reaction was allowed to proceed for three hours. Water (0.5 mL) was added, and concentration was carried out. Then, water (10 ml) was added to the solution, and extraction was carried out using ethyl acetate (10 ml,×2). Then, the organic layer was washed with water (10 mL) and saturated salt water (10 ml), and dehumidified with anhydrous magnesium sulfate. Subsequently, a crude product obtained by concentration was purified by column chromatography (silica gel, 70% ethyl acetate-hexane solution) to give acetic acid (1-methyl-1H-tetrazole-5-ylsulfanyl)methyl ester containing 1,2-hydrazinedicarboxylic acid diisopropyl ester as 610 mg of a colorless oily substance. Measurement of $^1$H-NMR showed that 406 mg of acetic acid (1-methyl-1H-tetrazole-5-ylsulfanyl) methyl ester (yield: 65%/glycolic acid methyl ester), and 204 mg of 1,2-hydrazinedicarboxylic acid diisopropyl ester were contained.

Example 18

Production of (1S,2S,5R)-1-(4-nitrobenzoyloxy)-2-isopropyl-5-methyl cyclohexanol: utilization for Mitsunobu reaction

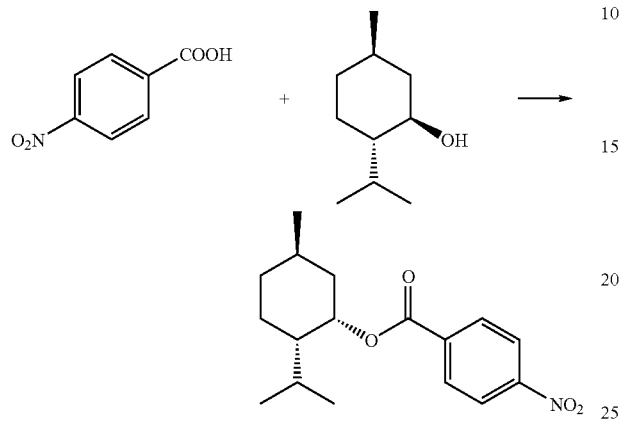

[Chem. 29]

After L-menthol (300 mg, 1.92 mmol), triphenylphosphine (605 mg, 2.30 mmol), 4-nitrobenzoic acid (385 mg, 2.30 mmol), and THF (12 ml) were added to a 50 ml flask, azodicarboxylic acid bis(2-methoxyethyl) ester (540 mg, 2.30 mmol) dissolved in THF (6 ml) was added dropwise thereto at 20° C., and the reaction was allowed to proceed for 17 hours. Water (0.5 ml) was added, and concentration was carried out. Then, water (10 ml) was added to the solution, and extraction was carried out using diethyl ether (10 ml,×2). Then, the organic layer was washed with water (10 mL) and saturated salt water (10 ml), and dehumidified with anhydrous magnesium sulfate. Subsequently, a crude product obtained by concentration was purified by column chromatography (silica gel, 5% ethyl acetate-hexane solution) to give (1S,2S,5R)-1-(4-nitrobenzoyloxy)-2-isopropyl-5-methyl cyclohexanol as a white solid substance (430 mg, yield: 73%/L-menthol).

Specific rotation: $[\alpha]_D^{20}$=+21.6 (c 1.02, MeOH).

Mp: 94.1-94.7° C.

IR (KBr): 2965, 2920, 2853, 1713, 1599, 1530, 1348, 1279, 1123, 1103, 1013, 920, 874, 839, 719 cm$^{-1}$.

$^1$H NMR (600 MHz, CDCl$_3$): δ 8.27 (dm, J=9.0 Hz, 2H), 8.18 (dm, J=9.0 Hz, 2H), 5.47 (d, J=2.0 Hz, 1H), 2.07 (ddd, J=14.4, 5.9, 4.7 Hz, 1H), 1.84 (m, 1H), 1.66 (m, 2H), 1.11 (m, 1H), 0.90 (d, J=5.9 Hz, 3H), 0.87 (d, J=7.1 Hz, 3H), 0.85 (d, J=7.1 Hz, 3H).

$^{13}$C NMR (100 MHz, CDCl$_3$): δ 163.99, 150.43, 136.37, 130.60, 123.55, 73.17, 46.92, 39.10, 34.71, 29.43, 26.82, 25.37, 22.10, 20.92, 20.75.

Elemental Analysis

Calculated value: C$_{17}$H$_{23}$NO$_4$: C, 66.86; H, 7.59; N, 4.59.

Measured value: C, 66.99; H, 8.11 N, 4.59.

Comparative Example 8

Comparative Example for Example 18 (Using Azodicarboxylic Acid Diisopropyl Ester)

After L-menthol (300 mg, 1.92 mmol), triphenylphosphine (605 mg, 2.30 mmol), 4-nitrobenzoic acid (387 mg, 2.30 mmol), and THF (12 ml) were added to a 50 ml flask, a 40% azodicarboxylic acid diisopropyl ester-toluene solution (1.21 ml, 2.30 mmol) dissolved in THF (6 ml) was added dropwise thereto at 20° C., and the reaction was allowed to proceed for 15 hours. Water (0.5 mL) was added, and concentration was carried out. Then, water (10 ml) was added to the solution, and extraction was carried out using diethyl ether (10 ml,×2). Then, the organic layer was washed with water (10 ml) and saturated salt water (10 ml), and dehumidified with anhydrous magnesium sulfate. Subsequently, a crude product obtained by concentration was purified by column chromatography (silica gel, 5% ethyl acetate-hexane solution) to give (1S,2S,5R)-1-(4-nitrobenzoyloxy)-2-isopropyl-5-methyl cyclohexanol as a white solid substance (423 mg, yield: 72%/L-menthol).

$^1$H NMR (600 MHz, CDCl$_3$): δ 8.27 (dm, J=9.0 Hz, 2H), 8.18 (dm, J=9.0 Hz, 2H), 5.47 (d, J=2.0 Hz, 1H), 2.07 (ddd, J=14.4, 5.9, 4.7 Hz, 1H), 1.84 (m, 1H), 1.66 (m, 2H), 1.11 (m, 1H), 0.90 (d, J=5.9 Hz, 3H), 0.87 (d, J=7.1 Hz, 3H), 0.85 (d, J=7.1 Hz, 3H).

Example 19

Production of 5,6-dihydrothiazolo[3,2-d]tetrazole: utilization for Mitsunobu reaction

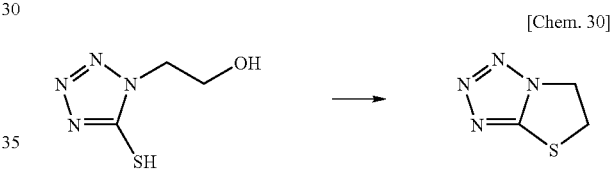

[Chem. 30]

After triphenylphosphine (649 mg, 2.46 mmol) and THF (105 ml) were added to a 300 mL flask, azodicarboxylic acid bis(2-methoxyethyl) ester (300 mg, 2.46 mmol) dissolved in THF (15 mL) was added dropwise thereto at 20° C. Subsequently, 1-(2-hydroxyethyl)-5-mercapto-1H-tetrazole (300 mg, 2.05 mmol) dissolved in THF (90 mL) was added dropwise thereto at 20° C., and the reaction was allowed to proceed for 39 hours. Water (0.5 mL) was added, and concentration was carried out. Then, water (10 ml) was added to the solution, and extraction was carried out using ethyl acetate (10 ml,×2). Then, the organic layer was washed with water (10 mL) and saturated salt water (10 ml), and dehumidified with anhydrous magnesium sulfate. Subsequently, a crude product obtained by concentration was recrystallized using isopropanol (3 mL) to give 5,6-dihydrothiazolo[3,2-d]tetrazole as a white powdered substance (83 mg, yield: 32%/1-(2-hydroxyethyl)-5-mercapto-1H-tetrazole).

Mp: 107.7-109.8° C.

IR (KBr): 3034, 2963, 1472, 1452, 1435, 1418, 1312, 1213, 1157, 1121, 1063, 955, 862, 712, 660, 546, 484 cm$^{-1}$.

$^1$H NMR (600 MHz, CDCl$_3$): δ 4.57 (t, J=7.6 Hz, 2H), 4.19 (t, J=7.6 Hz, 2H).

$^{13}$C NMR (100 MHz, CDCl$_3$): δ 161.94, 44.96, 37.55.

Calculated value: C$_3$H$_4$N$_4$S: C, 28.12; H, 3.15; N, 43.72; S, 25.02.

Measured value: C, 28.69; H, 3.32; N, 43.36; S, 24.30.

Example 20

Production of 15-pentadecanolactone: utilization for Mitsunobu reaction

[Chem. 31]

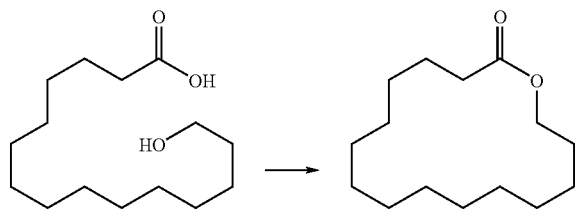

After triphenylphosphine (366 mg, 1.39 mmol) and THF (135 mL) were added to a 300 mL flask, azodicarboxylic acid bis(2-methoxyethyl) ester (367 mg, 1.39 mmol) dissolved in THF (30 mL) was added dropwise thereto at 20° C. Subsequently, 15-hydroxypentadecanoic acid (300 mg, 1.16 mmol) dissolved in THF (60 mL) was added dropwise thereto at 20° C., and the reaction was allowed to proceed for 12.5 hours. Water (0.5 mL) was added, and concentration was carried out. Then, water (15 ml) was added to the solution, and extraction was carried out using diethyl ether (15 ml,×2). Then, the organic layer was washed with water (15 mL) and saturated salt water (15 ml), and dehumidified with anhydrous magnesium sulfate. Subsequently, a crude product obtained by concentration was purified by column chromatography (silica gel, 5% ethyl acetate-hexane solution) to give 15-pentadecanolactone as a white solid substance (86 mg, yield: 31%/15-hydroxypentadecanoic acid).

Mp: 33.9-35.8° C.

IR (KBr): 2930, 2857, 1736, 1460, 1350, 1258, 1236, 1221, 1167, 1142, 1107, 1070, 719 cm$^{-1}$.

$^1$H NMR (600 MHz, CDCl$_3$): δ 4.11 (t, J=5.5 Hz, 2H), 2.30 (t, J=6.9 Hz, 2H), 1.66-1.58 (m, 4H), 1.39 (m, 2H), 1.32-1.29 (m, 18H).

$^{13}$C NMR (100 MHz, CDCl$_3$): δ 173.91, 63.84, 34.31, 28.29, 27.65, 27.02, 27.00, 26.78, 26.55, 26.20, 25.89, 25.78, 25.69, 24.99, 24.84.

Calculated value: C$_{15}$H$_{28}$O$_2$: C, 74.95; H, 11.74.
Measured value: C, 75.33; H, 12.16.

Example 21

Production of (R)-2-(4-nitrobenzoyloxy)octane: utilization for Mitsunobu reaction

[Chem. 32]

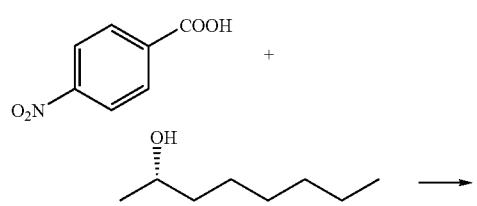

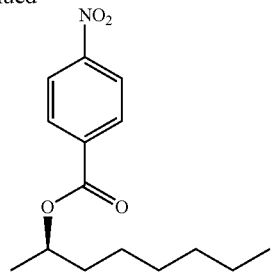

After (S)-2-octanol (300 mg, 2.30 mmol), triphenylphosphine (726 mg, 2.76 mmol), 4-nitrobenzoic acid (462 mg, 2.76 mmol), and THF (12 ml) were added to a 50 ml flask, azodicarboxylic acid bis(2-methoxyethyl) ester (648 mg, 2.76 mmol) dissolved in THF (6 ml) was added dropwise thereto at 20° C., and the reaction was allowed to proceed for 2.5 hours. Water (0.5 mL) was added, and concentration was carried out. Then, water (10 ml) was added to the solution, and extraction was then carried out using diethyl ether (10 ml,×2). Then, the organic layer was washed with water (10 mL) and saturated salt water (10 ml), and dehumidified with anhydrous magnesium sulfate. Subsequently, a crude product obtained by concentration was purified by column chromatography (silica gel, 10% ethyl acetate-hexane solution) to give (R)-2-(4-nitrobenzoyloxy)octane as a pale yellow liquid substance (579 mg, yield: 90%/(S)-2-octanol).

Specific rotation: [α]$_D^{20}$=-43.9 (c 1.21, MeOH).

IR (KBr): 3109, 2982, 2934, 1722, 1607, 1528, 1350, 1273, 1115, 1103, 1061, 1015, 874, 841, 719, 698 cm$^{-1}$.

$^1$H NMR (600 MHz, CDCl$_3$): δ 8.26 (d, J=8.6 Hz, 2H), 8.18 (d, J=8.6 Hz, 2H), 5.17 (m, 1H), 1.38-1.26 (m, 11H), 0.85 (t, J=6.5 Hz, 3H).

$^{13}$C NMR (100 MHz, CDCl$_3$): δ 163.96, 150.18, 136.06, 130.36, 120.19, 72.83, 35.71, 31.49, 28.91, 25.17, 22.35, 19.68, 13.79.

Comparative Example 9

Comparative Example for Example 21 (Using Azodicarboxylic Acid Diisopropyl Ester)

[Chem. 33]

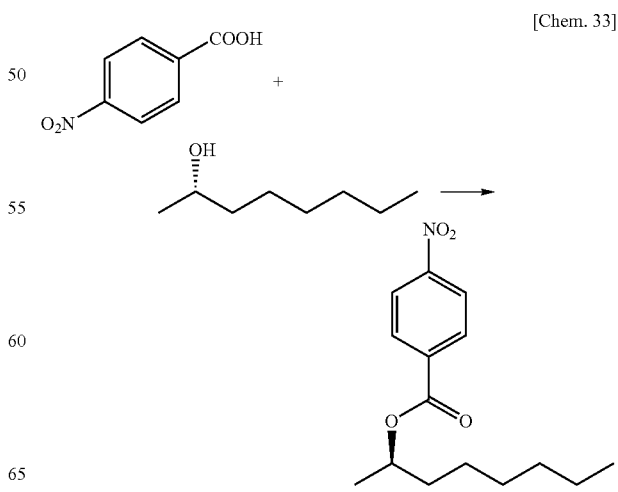

After (S)-2-octanol (300 mg, 2.30 mmol), triphenylphosphine (724 mg, 2.76 mmol), 4-nitrobenzoic acid (465 mg, 2.76 mmol), and THF (12 ml) were added to a 50 ml flask, a 40% azodicarboxylic acid diisopropyl ester-toluene solution (1.45 ml, 2.76 mmol) dissolved in THF (6 ml) was added dropwise thereto at 20° C., and the reaction was allowed to proceed for two hours. Water (0.5 mL) was added, and concentration was carried out. Then, water (10 ml) was added to the solution, and extraction was then carried out using diethyl ether (10 ml,×2). Then, the organic layer was washed with water (10 mL) and saturated salt water (10 ml), and dehumidified with anhydrous magnesium sulfate. Subsequently, a crude product obtained by concentration was purified by column chromatography (silica gel, 5% ethyl acetate-hexane solution) to give (R)-2-(4-nitrobenzoyloxy)octane as a pale yellow liquid substance (616 mg, yield: 96%/(S)-2-octanol).

$^1$H NMR (600 MHz, CDCl$_3$): δ 8.26 (d, J=8.6 Hz, 2H), 8.18 (d, J=8.6 Hz, 2H), 5.17 (m, 1H), 1.38-1.26 (m, 11H), 0.85 (t, J=6.5 Hz, 3H).

Example 22

Production of (R)-2-(4-nitrobenzoyloxy)octane: utilization for Mitsunobu reaction

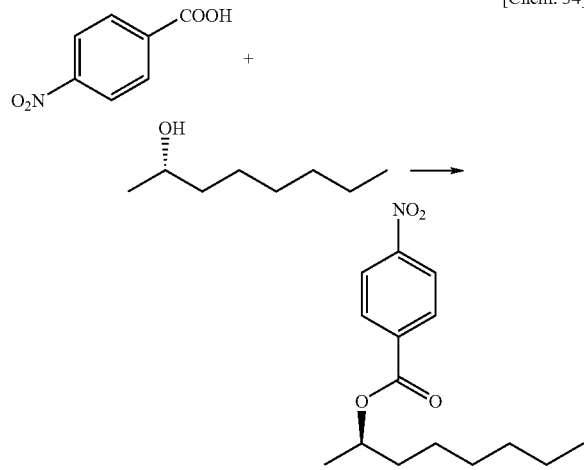

[Chem. 34]

After (S)-2-octanol (300 mg, 2.30 mmol), triphenylphosphine (726 mg, 2.76 mmol), 4-nitrobenzoic acid (462 mg, 2.76 mmol), and dichloromethane (12 ml) were added to a 50 ml flask, azodicarboxylic acid bis(2-methoxyethyl) ester (648 mg, 2.76 mmol) dissolved in dichloromethane (6 ml) was added dropwise thereto at 20° C., and the reaction was allowed to proceed for 1.5 hours. Water (10 mL) was added, and separation was carried out. Then, the aqueous layer was extracted using dichloromethane (10 mL,×1). The resulting organic layer was collectively washed with water (10 mL) and saturated salt water (10 ml), and dehumidified with anhydrous magnesium sulfate. Subsequently, a crude product obtained by concentration was purified by column chromatography (silica gel, 5% ethyl acetate-hexane solution) to give (R)-2-(4-nitrobenzoyloxy)octane as a pale yellow liquid substance (572 mg, yield: 89%/(S)-2-octanol).

$^1$H NMR (600 MHz, CDCl$_3$): δ 8.26 (d, J=8.6 Hz, 2H), 8.18 (d, J=8.6 Hz, 2H), 5.17 (m, 1H), 1.38-1.26 (m, 11H), 0.85 (t, J=6.5 Hz, 3H).

Example 23

Production of (R)-2-(4-nitrobenzoyloxy)octane: utilization for Mitsunobu reaction

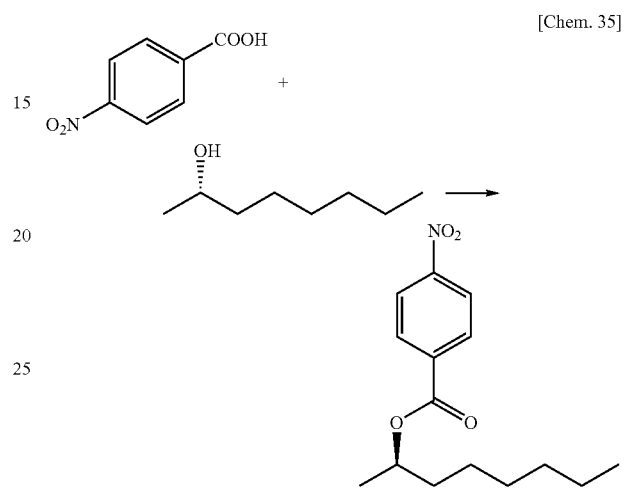

[Chem. 35]

After (S)-2-octanol (300 mg, 2.30 mmol), triphenylphosphine (725 mg, 2.76 mmol), 4-nitrobenzoic acid (463 mg, 2.76 mmol), and toluene (12 ml) were added to a 50 ml flask, azodicarboxylic acid bis(2-methoxyethyl) ester (648 mg, 2.76 mmol) dissolved in toluene (6 ml) was added dropwise thereto at 20° C., and the reaction was allowed to proceed for 3.5 hours. Water (10 mL) was added, and separation was carried out. Then, the aqueous layer was extracted using toluene (10 mL,×1). The resulting organic layer was collectively washed with water (10 mL) and saturated salt water (10 ml), and dehumidified with anhydrous magnesium sulfate. Subsequently, a crude product obtained by concentration was purified by column chromatography (silica gel, 5% ethyl acetate-hexane solution) to give (R)-2-(4-nitrobenzoyloxy)octane as a pale yellow liquid substance (615 mg, yield: 96%/(S)-2-octanol).

$^1$H NMR (600 MHz, CDCl$_3$): δ 8.26 (d, J=8.6 Hz, 2H), 8.18 (d, J=8.6 Hz, 2H), 5.17 (m, 1H), 1.38-1.26 (m, 11H), 0.85 (t, J=6.5 Hz, 3H).

Example 24

Production of (R)-2-(4-nitrobenzoyloxy)octane: utilization for Mitsunobu reaction

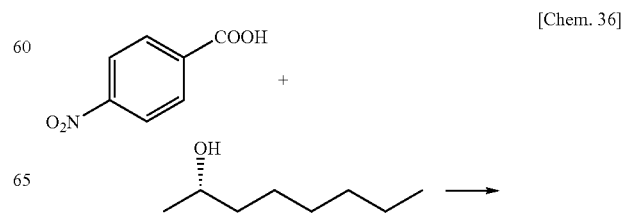

[Chem. 36]

-continued

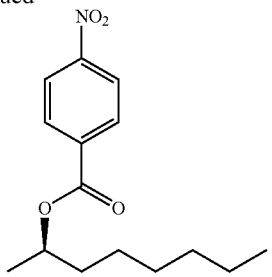

After (S)-2-octanol (300 mg, 2.30 mmol), triphenylphosphine (726 mg, 2.76 mmol), 4-nitrobenzoic acid (462 mg, 2.76 mmol), and acetonitrile (12 ml) were added to a 50 ml flask, azodicarboxylic acid bis(2-methoxyethyl) ester (648 mg, 2.76 mmol) dissolved in acetonitrile (6 ml) was added dropwise thereto at 20° C., and the reaction was allowed to proceed for 21 hours. Water (0.5 mL) was added, and concentration was carried out. Then, water (10 ml) was added to the solution, and extraction was carried out using diethyl ether (10 ml,×2). Then, the organic layer was washed with water (10 mL) and saturated salt water (10 ml), and dehumidified with anhydrous magnesium sulfate. Subsequently, a crude product obtained by concentration was purified by column chromatography (silica gel, 10% ethyl acetate-hexane solution) to give (R)-2-(4-nitrobenzoyloxy)octane as a pale yellow liquid substance (349 mg, yield: 54%/(S)-2-octanol).

$^1$H NMR (600 MHz, CDCl$_3$): δ 8.26 (d, J=8.6 Hz, 2H), 8.18 (d, J=8.6 Hz, 2H), 5.17 (m, 1H), 1.38-1.26 (m, 11H), 0.85 (t, J=6.5 Hz, 3H).

Example 25

Production of (R)-1-(4-nitrobenzoyloxy)-1-phenylethane: utilization for Mitsunobu reaction

[Chem. 37]

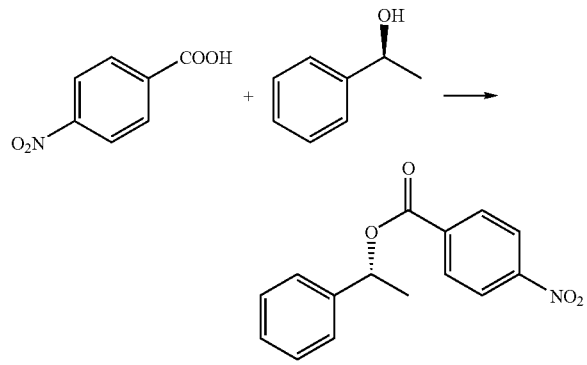

After (S)-1-phenylethyl alcohol (300 mg, 2.46 mmol), triphenylphosphine (771 mg, 2.95 mmol), 4-nitrobenzoic acid (494 mg, 2.95 mmol), and THF (12 ml) were added to a 50 ml flask, azodicarboxylic acid bis(2-methoxyethyl) ester (691 mg, 2.95 mmol) dissolved in THF (6 ml) was added dropwise thereto at 20° C., and the reaction was allowed to proceed for four hours. Water (0.5 mL) was added, and concentration was carried out. Then, water (10 ml) was added to the solution, and extraction was carried out using diethyl ether (10 ml,×2). Then, the organic layer was washed with water (10 mL) and saturated salt water (10 ml), and dehumidified with anhydrous magnesium sulfate. Subsequently, a crude product obtained by concentration was purified by column chromatography (silica gel, 5% ethyl acetate-hexane solution) to give (R)-1-(4-nitrobenzoyloxy)-1-phenylethane as a pale yellow liquid substance (559 mg, yield: 84%/(S)-1-phenylethyl alcohol).

Specific rotation: $[\alpha]_D^{20}$=−46.6 (c 1.09, MeOH).

IR (KCl, neat): 3111, 2955, 2930, 2859, 1719, 1607, 1528, 1466, 1348, 1280, 1113, 1103, 1015, 874, 841, 719 cm$^{-1}$.

$^1$H NMR (600 MHz, CDCl$_3$): δ 8.26 (d, J=8.9 Hz, 2H), 8.21 (d, J=8.9 Hz, 2H), 7.43 (d, J=7.6 Hz, 2H), 7.37 (t, J=7.6 Hz, 2H), 7.32 (d, J=7.6 Hz, 1H), 6.14 (q, J=6.9 Hz, 1H), 1.69 (d, J=6.9 Hz, 2H).

$^{13}$C NMR (100 MHz, CDCl$_3$): δ 163.79, 150.36, 140.88, 135.74, 130.62, 128.57, 128.15, 126.02, 123.39, 74.07, 22.10.

Comparative Example 10

Comparative Example for Example 25 (Using Azodicarboxylic Acid Diisopropyl Ester)

[Chem. 38]

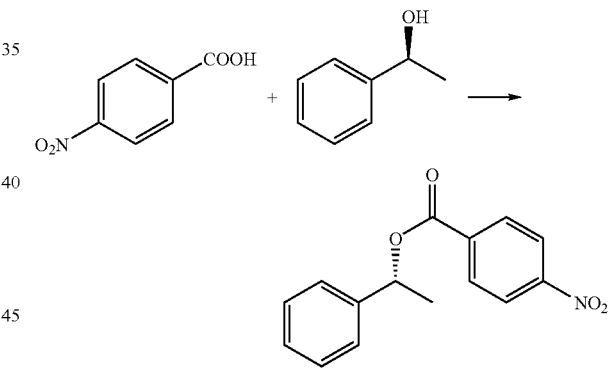

After (S)-1-phenylethyl alcohol (300 mg, 2.46 mmol), triphenylphosphine (773 mg, 2.95 mmol), 4-nitrobenzoic acid (493 mg, 2.95 mmol), and THF (12 ml) were added to a 50 ml flask, a 40% azodicarboxylic acid diisopropyl ester-toluene solution (1.55 ml, 2.76 mmol) dissolved in THF (6 ml) was added dropwise thereto at 20° C., and the reaction was allowed to proceed for four hours. Water (0.5 mL) was added, and concentration was carried out. Then, water (10 ml) was added to the solution, and extraction was carried out using diethyl ether (10 ml,×2). Then, the organic layer was washed with water (10 mL) and saturated salt water (10 ml), and dehumidified with anhydrous magnesium sulfate. Subsequently, a crude product obtained by concentration was purified by column chromatography (silica gel, 5% ethyl acetate-hexane solution) to give (R)-1-(4-nitrobenzoyloxy)-1-phenylethane as a pale yellow liquid substance (595 mg, yield: 89%/(S)-1-phenylethyl alcohol).

$^1$H NMR (600 MHz, CDCl$_3$): δ 8.26 (d, J=8.9 Hz, 2H), 8.21 (d, J=8.9 Hz, 2H), 7.43 (d, J=7.6 Hz, 2H), 7.37 (t, J=7.6 Hz, 2H), 7.32 (d, J=7.6 Hz, 1H), 6.14 (q, J=6.9 Hz, 1H), 1.69 (d, J=6.9 Hz, 2H).

Example 26

Production of
(R)-1-(4-nitrobenzoyloxy)-1-phenylethane:
utilization for Mitsunobu reaction

[Chem. 39]

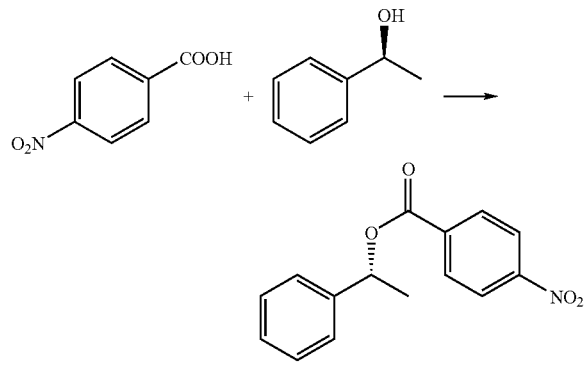

After (S)-1-phenylethyl alcohol (300 mg, 2.46 mmol), triphenylphosphine (772.5 mg, 2.95 mmol), 4-nitrobenzoic acid (494 mg, 2.95 mmol), and dichloromethane (12 ml) were added to a 50 ml flask, azodicarboxylic acid bis(2-methoxyethyl) ester (693 mg, 2.95 mmol) dissolved in dichloromethane (6 ml) was added dropwise thereto at 20° C., and the reaction was allowed to proceed for 46 hours. Water (10 mL) was added, and separation was carried out. Then, the aqueous layer was extracted using dichloromethane (10 mL,×1). The resulting organic layer was collectively washed with water (10 mL) and saturated salt water (10 ml), and dehumidified with anhydrous magnesium sulfate. Subsequently, a crude product obtained by concentration was purified by column chromatography (silica gel, 5% ethyl acetate-hexane solution) to give (R)-1-(4-nitrobenzoyloxy)-1-phenylethane as a pale yellow liquid substance (496 mg, yield: 74%/(S)-1-phenylethyl alcohol).

$^1$H NMR (600 MHz, CDCl$_3$): δ 8.26 (d, J=8.9 Hz, 2H), 8.21 (d, J=8.9 Hz, 2H), 7.43 (d, J=7.6 Hz, 2H), 7.37 (t, J=7.6 Hz, 2H), 7.32 (d, J=7.6 Hz, 1H), 6.14 (q, J=6.9 Hz, 1H), 1.69 (d, J=6.9 Hz, 2H).

Example 27

Production of
(R)-1-(4-nitrobenzoyloxy)-1-phenylethane:
utilization for Mitsunobu reaction

[Chem. 40]

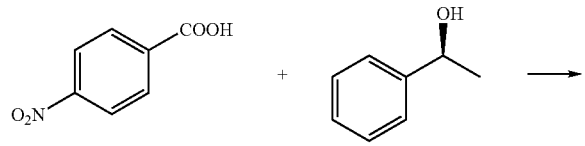

-continued

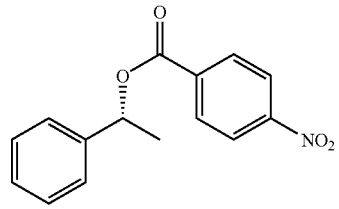

After (S)-1-phenylethyl alcohol (300 mg, 2.46 mmol), triphenylphosphine (772 mg, 2.95 mmol), 4-nitrobenzoic acid (493 mg, 2.95 mmol), and acetonitrile (12 ml) were added to a 50 ml flask, azodicarboxylic acid bis(2-methoxyethyl) ester (692 mg, 2.95 mmol) dissolved in acetonitrile (6 ml) was added dropwise thereto at 20° C., and the reaction was allowed to proceed for 40 hours. Water (0.5 mL) was added, and concentration was carried out. Then, water (10 ml) was added to the solution, and extraction was carried out using diethyl ether (10 ml,×2). Then, the organic layer was washed with water (10 mL) and saturated salt water (10 ml), and dehumidified with anhydrous magnesium sulfate. Subsequently, a crude product obtained by concentration was purified by column chromatography (silica gel, 5% ethyl acetate-hexane solution) to give (R)-1-(4-nitrobenzoyloxy)-1-phenylethane as a pale yellow liquid substance (202 mg, yield: 30%/(S)-1-phenylethyl alcohol).

$^1$H NMR (600 MHz, CDCl$_3$): δ 8.26 (d, J=8.9 Hz, 2H), 8.21 (d, J=8.9 Hz, 2H), 7.43 (d, J=7.6 Hz, 2H), 7.37 (t, J=7.6 Hz, 2H), 7.32 (d, J=7.6 Hz, 1H), 6.14 (q, J=6.9 Hz, 1H), 1.69 (d, J=6.9 Hz, 2H).

Example 28

Production of
(R)-1-(4-nitrobenzoyloxy)-1-phenylethane:
utilization for Mitsunobu reaction

[Chem. 41]

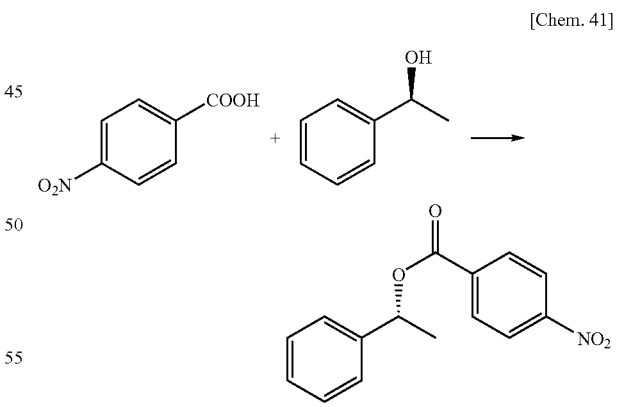

After (S)-1-phenylethyl alcohol (176 mg, 1.43 mmol), triphenylphosphine (449.8 mg, 1.72 mmol), 4-nitrobenzoic acid (288 mg, 1.72 mmol), and toluene (7 ml) were added to a 50 ml flask, azodicarboxylic acid bis(2-methoxyethyl) ester (403 mg, 1.72 mmol) dissolved in toluene (3.5 ml) was added dropwise thereto at 20° C., and the reaction was allowed to proceed for 6 hours. Water (10 mL) was added, and separation was carried out. Then, the aqueous layer was extracted using toluene (10 mL,×1). The resulting organic layer was collectively washed with water (10 mL) and saturated salt water (10 ml), and dehumidified with anhydrous magnesium sulfate. Subsequently, a crude product obtained by concentration was purified by column chromatography (silica gel, 5% ethyl acetate-hexane solution) to give (R)-1-(4-nitrobenzoyloxy)-1-phenylethane as a pale yellow liquid substance (352 mg, yield: 91%/(S)-1-phenylethyl alcohol).

$^1$H NMR (600 MHz, CDCl$_3$): δ 8.26 (d, J=8.9 Hz, 2H), 8.21 (d, J=8.9 Hz, 2H), 7.43 (d, J=7.6 Hz, 2H), 7.37 (t, J=7.6 Hz, 2H), 7.32 (d, J=7.6 Hz, 1H), 6.14 (q, J=6.9 Hz, 1H), 1.69 (d, J=6.9 Hz, 2H)

INDUSTRIAL APPLICABILITY

The present invention can be applied to the Mitsunobu reaction, and can be used as an oxidizing agent, and a starting material for various synthesis processes.

What is claimed is:

1. A method for producing an azodicarboxylic acid bis(2-alkoxyethyl) ester compound, comprising the steps of:
    (a): reacting hydrazine with a halocarbonic acid (2-alkoxyethyl) ester compound represented by formula (2):

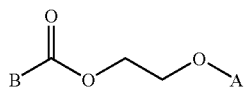
(2)

wherein A represents an alkyl group having 1 to 10 carbon atoms, and B represents a halogen atom, to give a 1,2-hydrazinedicarboxylic acid bis(2-alkoxyethyl) ester compound represented by formula (3):

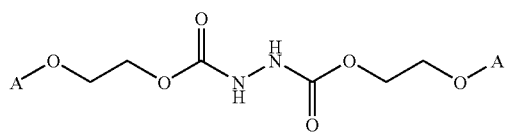
(3)

wherein A is as defined above; and
    (b): oxidizing the 1,2-hydrazinedicarboxylic acid bis(2-alkoxyethyl) ester compound represented by formula (3):

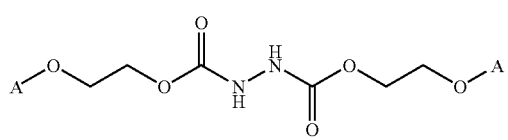
(3)

wherein A is as defined above, to give an azodicarboxylic acid bis(2-alkoxyethyl) ester compound represented by formula (1):

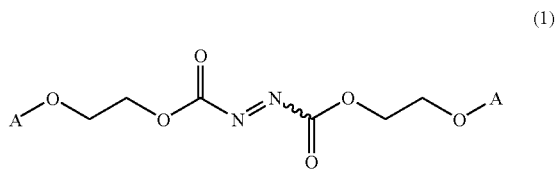
(1)

wherein A represents an alkyl group having 1 to 10 carbon atoms.

2. A 1,2-hydrazinedicarboxylic acid bis(2-alkoxyethyl) ester compound represented by formula (3):

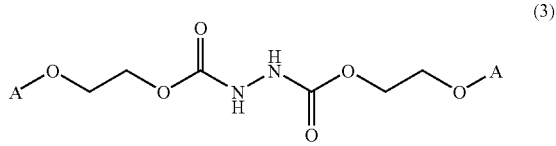
(3)

wherein A represents an alkyl group having 1 to 10 carbon atoms.

3. The compound according to claim 2, wherein the alkyl group is a methyl group.

4. A method for producing a 1,2-hydrazinedicarboxylic acid bis(2-alkoxyethyl) ester compound, comprising the step of:
    (a): reacting hydrazine with a halocarbonic acid (2-alkoxyethyl) ester compound represented by formula (2):

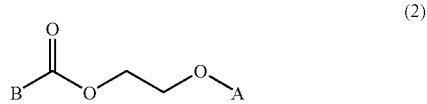
(2)

wherein A represents an alkyl group having 1 to 10 carbon atoms, and B represents a halogen atom, to give a 1,2-hydrazinedicarboxylic acid bis(2-alkoxyethyl) ester compound represented by formula (3):

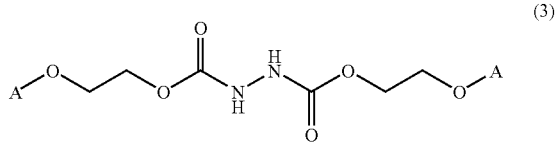
(3)

wherein A is as defined above.

* * * * *